(12) United States Patent
Mattson et al.

(10) Patent No.: US 8,414,911 B2
(45) Date of Patent: Apr. 9, 2013

(54) PHOTOCHEMICAL THERAPY TO AFFECT MECHANICAL AND/OR CHEMICAL PROPERTIES OF BODY TISSUE

(75) Inventors: Matthew S. Mattson, Pasadena, CA (US); Julia A. Kornfield, Pasadena, CA (US); Daniel M. Schwartz, San Francisco, CA (US); Robert K. Maloney, Palisades, CA (US); Robert H. Grubbs, South Pasadena, CA (US)

(73) Assignees: The Regents of the University of California, Oakland, CA (US); California Institute of Technology, Pasadena, CA (US)

( * ) Notice: Subject to any disclaimer, the term of this patent is extended or adjusted under 35 U.S.C. 154(b) by 773 days.

(21) Appl. No.: 11/923,575

(22) Filed: Oct. 24, 2007

(65) Prior Publication Data
US 2008/0114283 A1     May 15, 2008

Related U.S. Application Data

(60) Provisional application No. 60/853,949, filed on Oct. 24, 2006, provisional application No. 60/954,541, filed on Aug. 7, 2007.

(51) Int. Cl.
*A61F 2/00* (2006.01)
*A61K 31/74* (2006.01)
(52) U.S. Cl. .................... 424/427; 424/78.08
(58) Field of Classification Search .......... 604/20, 604/521; 606/6; 424/9.5, 427, 78.08
See application file for complete search history.

(56) References Cited

U.S. PATENT DOCUMENTS

| 6,161,544 A | 12/2000 | DeVore et al. |
| 6,478,792 B1 | 11/2002 | Hansel |
| 2005/0271590 A1* | 12/2005 | Schwartz et al. ............. 424/9.5 |
| 2006/0276777 A1* | 12/2006 | Coroneo ........................ 606/5 |

FOREIGN PATENT DOCUMENTS

| WO | WO 2005/110397 | 11/2005 |
| WO | 2007001926 A2 | 1/2007 |

OTHER PUBLICATIONS

International Preliminary Report on Patentability issued Apr. 29, 2009, (Published Apr. 29, 2009), during the prosecution of International Application No. PCT/US2007/82435.
International Search Report issued Mar. 24, 2008, (Published Jun. 19, 2008) during the prosecution of International Application No. PCT/US2007/82435.
Wollensak, "Crosslinking Treatment of Progressive Keratoconus: New Hope," Current opinion in Ophthalmology. vol. 17(4): 356-360. Aug. 2006. Abstract.
Written Opinion issued Mar. 24, 2008, (Published Apr. 24, 2009) during the prosecution of International Application No. PCT/US2007/82435.

(Continued)

*Primary Examiner* — Kevin C Sirmons
*Assistant Examiner* — Brandy C Scott
(74) *Attorney, Agent, or Firm* — Rudy J. Ng; Carol L. Francis; Bozicevic, Field & Francis LLP

(57) ABSTRACT

The disclosure concerns altering the mechanical and/or chemical property of a body tissue, particularly an ocular tissue. In specific cases, it concerns altering or stabilizing the shape of the cornea, such as in a subject suffering or at risk for ectasia or keratoconus. In other specific cases, it concerns strengthening the sclera in a subject suffering or at risk for myopia. The invention employs light irradiation of a photoactivatable compound, such as one that applies crosslinking to the tissue, for example.

50 Claims, 14 Drawing Sheets

OTHER PUBLICATIONS

Ehlers et al., "Factors affecting therapeutic concentration of topical aminocaproic acid in traumatic hyphema", Investigative Ophthalmology & Visual Science, vol. 31, 2389-2394, 1990.

Spoerl et al., "Artificial stiffening of the cornea by induction of intrastromal cross-links", Der Ophthalmologe 94, 902-906, 1997.

Spoerl et al., "Techniques for stiffening the cornea", Journal of Refactive Surgery 15, 711-713, 1999.

Tessier et al., "Rigidification of Corneas Treated In Vitro With Glyceraldehyde: Characterization of Two Novel Crosslinks and Two Chromophores", Invest Ophthalmol Vis Sci 2002;43, U892-U892.

Wollensak et al., "Collagen crosslinking of human and porcine sclera", Journal of Cataract and Refactive Surgery, vol. 30, Issue 3, 689-695, 2004.

Wollensak et al., "Cross-linking of scleral collagen in the rabbit using riboflavin and UVA", Acta Ophthalmol Scand. 2005; 83(4):477-82.

Wollensak et al., "Crosslinking treatment of progressive keratoconus: new hope.", Current Opinion in Opthalmology 17, 356-360, 2006.

Wollensak et al., "Hydration behavior of porcine cornea crosslinked with riboflavin and ultraviolet", A. J. Cataract Refract Surg. 2008;33(3):516-21.

Yang et al., "3-D Histomorphometry of the Normal and Early Glaucomatous Monkey Optic Nerve Head: Lamina Cribrosa and Peripapillary Scleral Position and Thickness", Invest. Opthalmol Vis. Sci. 2007; 48:4597-4607.

Singapore Written Opinion issued May 19, 2010, during the prosecution of SG Application No. 200902255-9.

Singapore Search Report issued May 27, 2010, during the prosecution of SG Application No. 200902255-9.

\* cited by examiner

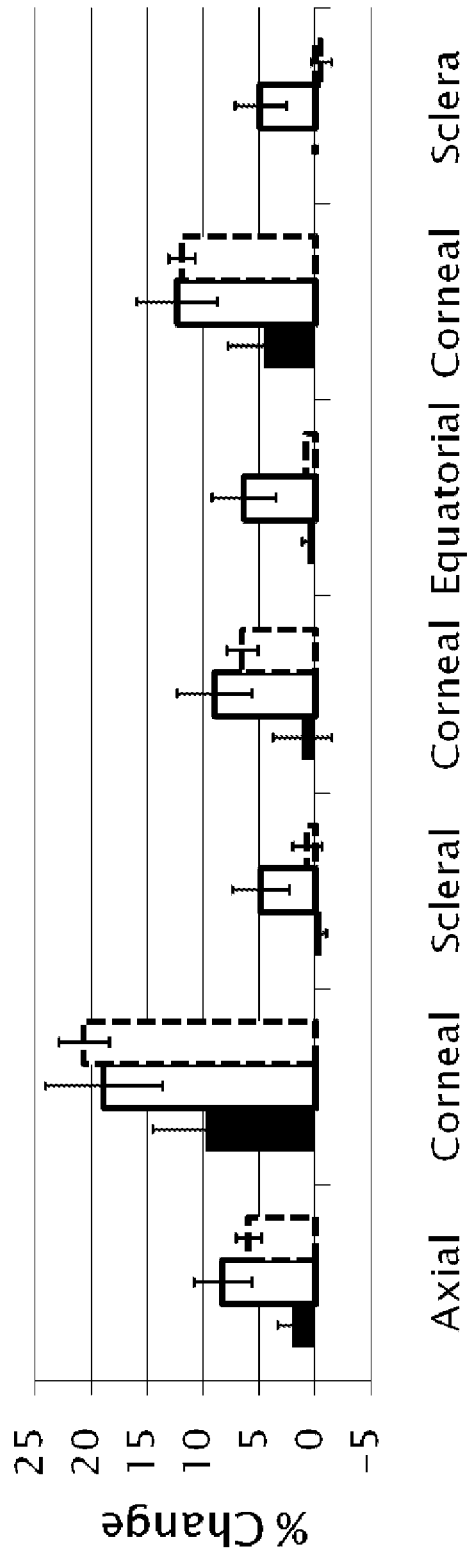

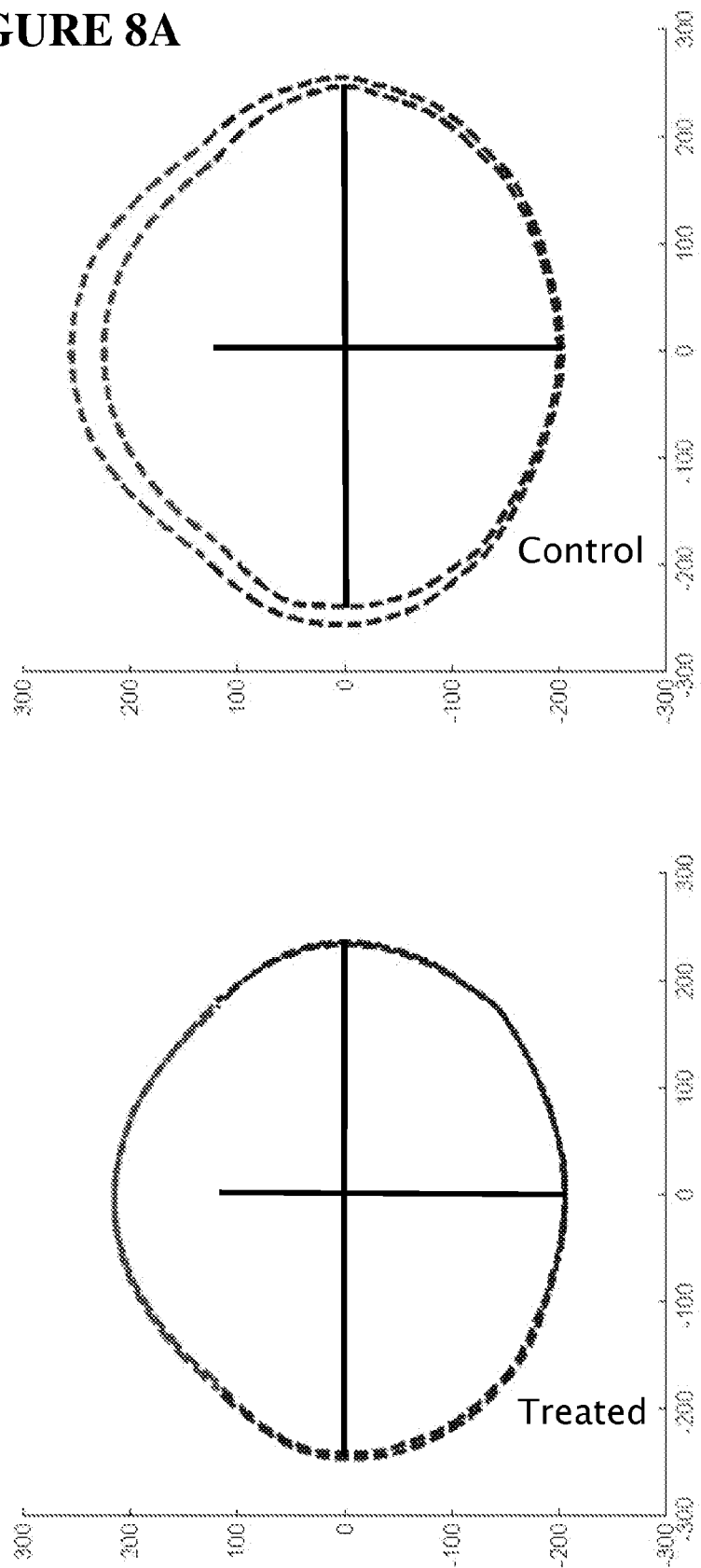

FIGURE 9
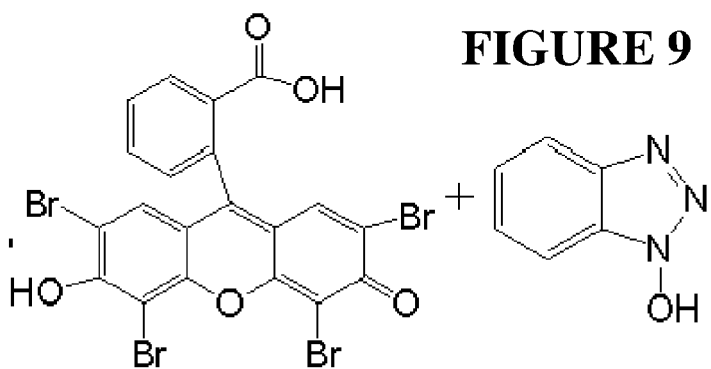
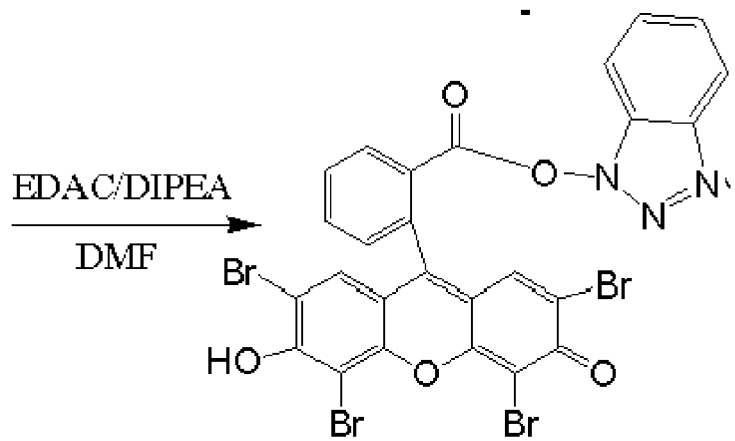
Intermediate 1
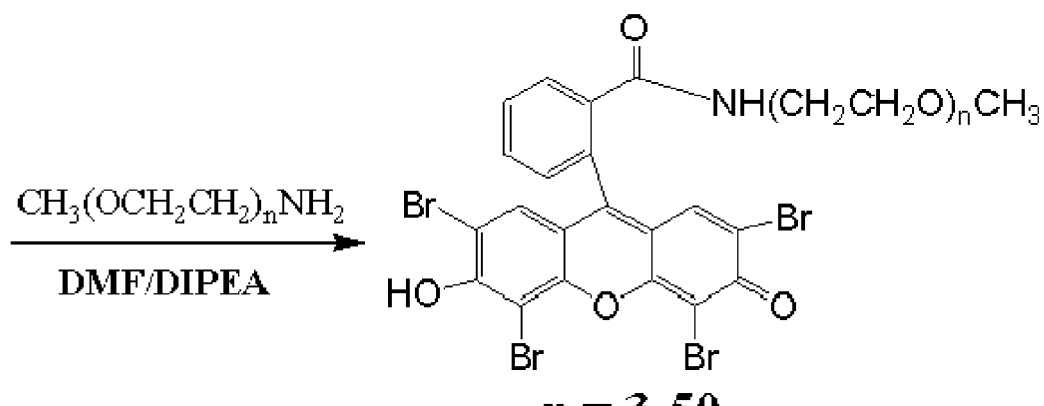
n = 3-50
Compound 1

FIGURE 11B
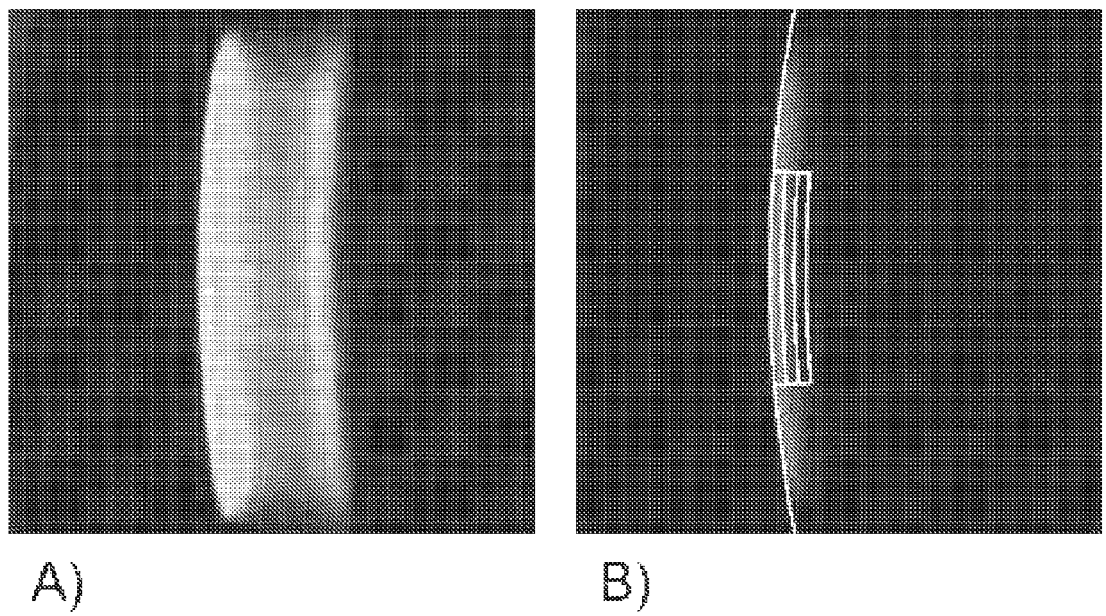
A)  B)
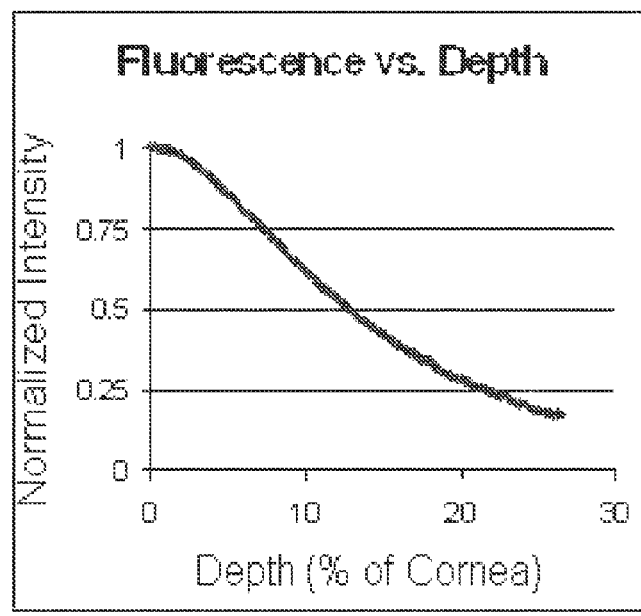
C)

PHOTOCHEMICAL THERAPY TO AFFECT MECHANICAL AND/OR CHEMICAL PROPERTIES OF BODY TISSUE

RELATED APPLICATIONS

This application claims the benefit under 35 U.S.C. 119(e) of U.S. Provisional Patent Application No. 60/853,949 filed 24 Oct. 2006 and the benefit under 35 U.S.C. 119(e) of U.S. Provisional Patent Application No. 60/954,541 filed 7 Aug. 2007.

STATEMENT REGARDING FEDERALLY SPONSORED RESEARCH OR DEVELOPMENT

The present invention was developed at least in part with funds from National Institutes of Health grant R41EY017484. The United States Government may have certain rights in the invention.

TECHNICAL FIELD

The fields of the invention concern medicine, anatomy, cell biology, or molecular biology, for example. In particular, the field of the invention concerns ocular medicine, including ophthalmology.

BACKGROUND OF THE INVENTION

Keratoconus

Keratoconus (Rabinowitz, 1998; Krachmer et al., 1994; Bron, 1988) is the most common corneal dystrophy, affecting 1 in 2000 persons. Keratoconus results in corneal thinning and is named for the conical shape that the cornea develops. The progressive distortion of corneal shape usually becomes noticeable in early adulthood, causing increasingly severe astigmatism, myopia, and higher-order aberrations that become difficult to correct by spectacles or contact lenses. When distortions reach the point that refractive correction is no longer possible, corneal transplant is the only option.

Methods to strengthen the cornea and prevent progression of the disease are needed. There is evidence that crosslinking of corneal collagen that occurs in diabetes provides protection against keratoconus (Seiler et al., 2000) Additionally, groups have reported strengthening of the cornea through common crosslinking agents. Glyceraldehyde has been used as a corneal crosslinking agent, but it has significant toxicity. An approach to minimize toxicity of the drug itself uses topically applied riboflavin, which is then subjected to ultraviolet light (Tae et al., 2000; Tessier et al., 2002; Spoerl and Seiler, 1999; Spoerl et al., 1997; Wollensak et al., 2003) Longitudinal studies over 3 years or more have shown that treating the cornea with UV activated crosslinking can provide sufficient structural reinforcement to slow or halt the progression of keratoconus (Wollensak et al., 2003; Wollensak, 2006). While uv-activated riboflavin represents a possible advance in the treatment of keratoconus, it would be optimal to overcome the limitations of this treatment. Riboflavin/UV requires painful removal of the epithelium with risk of long-term ulceration; it uses UV light, with inherent risk of damage to ocular tissues; it requires 30 minutes of irradiation which is clinically undesirable and increases the risk of corneal infection. Therefore, clinically, there is a need for a treatment that prevents disease progression and remedies the shortcomings of uv-activated riboflavin treatment. In particular, there is a need in the art of ocular medicine for one or more of the following: 1) improved drug; 2) improved administration of drug; and 3) improved irradiation protocol.

Myopia

Myopia affects 30% of the population in the U.S. and Europe, and 70-90% of the population in some Asian countries (Lin L L, Shih Y F, Hsiao C K, Chen C J, Lee L A, Hung P T. Epidemiologic study of the prevalence and severity of myopia among schoolchildren in Taiwan in 2000. J Formos Med. Assoc. 2001; 100(10):684-91; Chow, Y. C., Dhillon, B. B., Chew, P. T. & Chew, S. J. Refractive errors in Singapore medical students. Singapore Medical Journal 45, 470-474 (1990); Wong, T. Y., Foster, P. J., Hee, J. J., Ng, T. P., Tielsch, J. M., Chew, S. J., Johnson, G. J. & Seah, S. K. Prevalence and risk factors for refractive errors in adult Chinese in Singapore. Investigative Ophthalmology & Visual Science 41, 2486-2494 (2000)). High myopia of greater than 8 diopters affects 0.2-0.4% of the US population and up to 1% of the population in Asian countries (Sperduto, R. D., Seigel, D. D., Roberts, J. J. & Rowland, M. M. Prevalence of myopia in the United States. 405-407 (1983); Tokoro, T. On the definition of pathologic myopia in group studies. Acta Opthalmol Suppl 185, 107-108 (1998)). Indeed, degenerative myopia is the leading cause of untreatable blindness in China, Taiwan, and Japan, and is ranked $7^{th}$ in the United States (Xu L, Wang Y, Li Y, Wang Y, Cui T, Li J, Jonas J B. Causes of blindness and visual impairment in urban and rural areas in Beijing: the Beijing Eye Study. Ophthalmology. 2006 113:1134.e1-11; Hsu W M, Cheng C Y, Liu J H, Tsai S Y, Chou P. Prevalence and causes of visual impairment in an elderly Chinese population in Taiwan: the Shihpai Eye Study. Ophthalmology. 2004; 111(1):62-9; Iwase A, Araie M, Tomidokoro A, Yamamoto T, Shimizu H, Kitazawa Y; Tajimi Study Group. Prevalence and causes of low vision and blindness in a Japanese adult population: the Tajimi Study. Ophthalmology. 2006; 113(8):1354-62; Curtin, B. J. The myopias: basic science and clinical management (Lippincott Williams & Wilkins, 1985).

In degenerative myopia there is progressive axial elongation of the eye. The excessive axial enlargement in degenerative myopia causes stretching and thinning of the ocular coats (sclera and chorioretinal tissues). Because this stretching and thinning occurs preferentially in the posterior pole and involves the macula, eyes with degenerative myopia are subject to visual loss. The causes of scleral thinning and stretching in degenerative myopia are incompletely understood, but enhanced turnover of scleral collagen and alteration of scleral glycosaminoglycans are contributory in the disease. As the mechanical properties of the sclera are altered in myopia, the eye is prone to stretching due to the load effect of intraocular pressure. When the sclera stretches in pathologic myopia, the adjacent retina and choroid are also stretched, and the stretching is disproportionate in the macular region where scleral and retinal thinning is maximal. This leads to formation of a focal out-pouching, or staphyloma. As the macular tissues stretch, retinal cells atrophy, causing irreversible visual loss. While visual loss from macular atrophy and choroidal neovascularization are most common in degenerative myopia, patients with this disease are also more prone to retinal detachment and macular hole formation. Although a large population is affected by this disease worldwide, there is currently no effective method to arrest progression and reduce the rate of visual loss.

Refractive errors induced by progressive myopia are readily corrected by spectacles, contact lenses, corneal refractive surgery, or intraocular lenses, these modalities do not prevent visual loss induced by stretching of chorioretinal tissues. Furthermore, current means to treat choroid neovascularization in degenerative myopia, such as photodynamic therapy, are minimally effective (Blinder, K. J., Blumenkranz, M. S., Bressler, N. M., Bressler, S. B., Donati, G., Lewis, H., Lim, J. I., Menchini, U., Miller, J. W., Mones, J. M., Potter, M. J., Pournaras, C., Reaves, A., Rosenfeld, P., Schachat, A. P., Schmidt-Erfurth, U., Sickenberg, M., Singerman, L. J., Slakter, J., Strong, H. A., Virgili, G. & Williams, G. A. Verteporfin therapy of subfoveal choroidal neovascularization in pathologic myopia-2-year results of a randomized clinical Trial—VIP report no. 3. Ophthalmology 110, 667-673 (2003)). A role for anti-vascular endothelial growth factor (VEGF) therapy, such as Lucentis®, for treatment of choroidal neovascularization has not yet been established. Various attempts have been made to arrest progression of myopia, including the use of scleroplasty, scleral reinforcement, and even an attempt to polymerize foam around the eye (Avetisov, E. S., Tarutta, E. P., Iomdina, E. N., Vinetskaya, M. I. & Andreyeva, L. D. Nonsurgical and surgical methods of sclera reinforcement in progressive myopia. Acta Ophthalmologica Scandinavica 75, 618-623 (1997); Chua, W. H., Tan, D., Balakrishnan, V. & Chan, Y. H. Progression of childhood myopia following cessation of atropine treatment. Investigative Ophthalmology & Visual Science 46 (2005); Tarutta, Y. P., Iomdina, Y. N., Shamkhalova, E. S., Andreyeva, L. D. & Maximova, M. V. Sclera Fortification In Children At A High-Risk Of Progressive Myopia. Vestnik Oftalmologii 108, 14-17 (1992); Politzer, M. Experiences In Medical-Treatment Of Progressive Myopia. Klinische Monatsblatter Fur Augenheilkunde 171, 616-619 (1977); Belyaev, V. S. & Ilyina, T. S. Late Results Of Scleroplasty In Surgical Treatment Of Progressive Myopia. Eye Ear Nose And Throat Monthly 54, 109-113 (1975); Chauvaud, D., Assouline, M. & Perrenoud, F. Scleral reinforcement. Journal Francais D Ophtalmologie 20, 374-382 (1997); Jacob, J. T., Lin, J. J. & Mikal, S. P. Synthetic scleral reinforcement materials.3. Changes in surface and bulk physical properties. Journal Of Biomedical Materials Research 37, 525-533 (1997); Korobelnik, J. F., D'Hermies, F., Chauvaud, D., Legeais, J. M., Hoang-Xuan, T. & Renard, G. Expanded polytetrafluoroethylene episcleral implants used as encircling scleral buckling—An experimental and histopathological study. Ophthalmic Research 32, 110-117 (2000); Mortemousque, B., Leger, F., Velou, S., Graffan, R., Colin, J. & Korobelnik, J. F. S/e-PTFE episcleral buckling implants: An experimental and histopathologic study. Journal Of Biomedical Materials Research 63, 686-691 (2002); Jacoblabarre, J. T., Assouline, M., Conway, M. D., Thompson, H. W. & McDonald, M. B. Effects Of Scleral Reinforcement On The Elongation Of Growing Cat Eyes. Archives Of Ophthalmology 111, 979-986 (1993)). Largely because these modalities remain unproven in well controlled clinical trials, none has been widely adopted to manage patients with degenerative myopia. Other therapies, such as eye drops (Chua W H, Balakrishnan V, Chan Y H, Tong L, Ling Y, Quah B L, Tan D. Atropine for the treatment of childhood myopia. Ophthalmology. 2006 December; 113(12):2285-91; Siatkowski R M, Cotter S, Miller J M, Scher C A, Crockett R S, Novack G D; US Pirenzepine Study Group.Safety and efficacy of 2% pirenzepine ophthalmic gel in children with myopia: a 1-year, multicenter, double-masked, placebo-controlled parallel study. Arch Ophthalmol. 2004; 122(11):1667-74), eye exercises (Khoo C Y, Chong J, Rajan U. A 3-year study on the effect of RGP contact lenses on myopic children. Singapore Med J 1999; 40:230-7), and contact lens therapy (Shih Y F, Lin L L, Hwang C Y, et al. The effects of qi-qong ocular exercise on accommodation. Clin J Physiol 1995; 38:35-42) have either minimal or no proven efficacy. Were it possible to retard or prevent abnormal axial elongation of the globe in degenerative myopia, visual loss might be prevented.

The excessive axial enlargement of the globe that occurs in degenerative myopia occurs preferentially in the posterior pole in the macula. The causes of scleral thinning and stretching in degenerative myopia are incompletely understood, but reduction of collagen fibril diameter, enhanced turnover of scleral collagen, and alteration of scleral glycosaminoglycans are contributory factors (McBrien, N. A. & Gentle, A. Role of the sclera in the development and pathological complications of myopia. Progress In Retinal And Eye Research 22, 307-338 (2003)). As the mechanical properties of the sclera are altered in myopia, the eye is prone to stretching due to the load effect of intraocular pressure. Sufficiently increasing the tensile strength, or modulus, of the sclera would prevent ocular enlargement and reduce progression of myopia. Such a therapy will be useful not only in patients with incipient degenerative myopia, but also in patients with early onset myopia to prevent progression to higher magnitude refractive errors.

Currently, there are no proven means to prevent the excessive ocular enlargement that occurs in degenerative myopia. Were it possible to retard or prevent ocular enlargement, progression of myopia could be diminished and visual loss prevented at least in part. Were the progressive stretching of the sclera in the macular region to be arrested, retinal stretching or further retinal stretching would not occur, and vision could be preserved. Efforts have been made to support the macular region with an external donor scleral or synthetic polymer band placed around the eye, but this has not been proven to be effective. Artificially increasing the tensile strength or modulus of the sclera itself is a means to prevent ocular enlargement and reduce progression of myopia.

Wollensak and Speorl have reported use of collagen cross-linking agents, including glutaraldehyde, glyceraldehyde, and riboflavin-UVA treatment, to strengthen both human and porcine sclera in vitro (Wollensak, G. & Spoerl, E. Collagen crosslinking of human and porcine sclera. Journal Of Cataract And Refractive Surgery 30, 689-695 (2004)). Glutaraldehyde, glyceraldehyde, and riboflavin-UVA treatments increased Young's modulus by 122%, 34%, and 29% respectively compared to untreated controls. Since they are not light-activated, the authors report that it might be difficult to spatially control the cross linking effects of both glutaraldehyde and glyceraldehyde. Unwanted cross-linking of collagen in vascular and neural structures might have particularly untoward effects. Use of light activated riboflavin would seem preferable in this regard; however, UVA light is potentially cytotoxic and comparable exposures in the cornea to treat keratoconus require 30 minute irradiations (Wollensak G. Crosslinking treatment of progressive keratoconus: new hope. Curr Opin Ophthalmol. 2006; 17(4):356-60). While cross-linking of scleral stromal components in the posterior pole would increase scleral modulus and potentially arrest myopic progression, there remains a need for a non-toxic cross-linking agent that could be activated using short exposure to a less toxic light source.

U.S. Published Application No. 20050271590, the contents of which are incorporated herein by reference, discloses methods of using crosslinking chemicals to covalently connect scleral collagen and/or other scleral proteins to increase scleral tensile strength or modulus. This approach utilizes chemical crosslinkers, some with undesirable toxicity profiles, by caging the chemicals in photo-labile structures which are disrupted to release the crosslinker chemicals in a controlled manner, thereby limiting the area of exposure and in some instances toxicity effects.

Given the limitations of current therapies for treating keratoconus and myopia, new therapies without such limitations are needed. The present invention fulfills this need.

SUMMARY OF THE INVENTION

The present invention concerns a therapy for affecting one or more mechanical and/or chemical properties of a body tissue in an individual. In specific embodiments, the present invention concerns one or more photochemical therapies for affecting one or more mechanical and/or chemical properties of a body tissue in an individual. The therapy may be for any tissue in the body, including at least an ocular tissue, a blood vessel wall, aveolar structures (e.g. in COPD patients), and damaged heart tissue, e.g., for the mitigation of dilated cardiomyopathies. In particular embodiments, the therapy is used for an ocular tissue. Exemplary ocular tissues include at least the cornea, sclera, optic nerve, trabecular meshwork, conjunctiva, choroid, and subretinal space.

In specific embodiments, the present invention employs a therapy that is an improvement upon particular therapies for certain ocular applications. In further specific embodiments, the present invention improves upon uv-irradiation treatments for crosslinking of tissues, such as the cornea or sclera, for example. Such a treatment would have one or more of the following exemplary specifications: 1) a photoinitiator compound that can be activated with visible light to affect the mechanical and/or chemical properties of a tissue, such as improve the mechanical properties of the cornea to resist progressive ectasia, for example; 2) the photoinitiator compound may be introduced with minimal pain and/or minimal risk; 3) the photoinitiator compound is non-toxic to ocular structures; 4) photoinitiator compound activation occurs with safe levels of irradiation; 5) photoinitiator compound activation occurs with less than or equal to 30 minutes irradiation, for example.

In particular embodiments of the invention, the present invention provides one or more of the following needs: 1) an effective photoinitiator compound for strengthening a tissue (such as the cornea or sclera, for example) is demonstrated that has low toxicity and is activated by visible light; 2) improved photoinitiator compounds or derivatives thereof that are capable of administration routes that obviate the need to remove epithelium (such as for keratoconus treatment of a cornea) are described, including, for example, (a) topical application of drug that itself, or after modification, can cross the corneal epithelium in sufficient concentration to reach the corneal stroma in a therapeutically effective amount; and/or (b) injection of drug into the stroma using a fine-gauge needle; and/or 3) reduced irradiation duration using light applied for about 30 minutes or less is demonstrated to affect the tissue, such as to stabilize the shape of the cornea, for example.

Exemplary applications of the present invention for ocular needs are provided. In particular embodiments, the invention is employed for the cornea, including the following: preventing the need for cornea transplant (keratoplasty) by halting progression of keratoconus and other corneal ectasias such as post-LASIK ectasia, pellucid marginal degeneration; enabling patients with keratoconus or other corneal degenerations to safely undergo refractive surgery; and/or stabilizing corneal shape after refractive surgery, particularly if keratoconus becomes manifested afterward. The present invention also provides means for stabilization of tissue anywhere in the eye, including for example the sclera, using light-activated crosslinking with visible light.

Although in particular embodiments the invention employs visible light, in alternative embodiments, the present invention utilize ultraviolet or infrared light. In further specific embodiments, the present invention also applies to photoinitiator activation using two-photon or multi-photon activation.

In certain aspects of the invention, the photoinitiator compound is employed to affect crosslinking among the constituent molecules in an endogenous tissue in a subject.

Some embodiments herein are a method of altering a mechanical and/or chemical property of a tissue in a subject comprising the steps of:
  a) providing a photoinitiator compound to a tissue of the subject, and
  b) activating the photoinitiator compound by a visible light irradiation of the tissue,
  whereby the photoinitiator compound directly alters a mechanical and/or chemical property of the tissue.

Some embodiments herein are the method of paragraph [0024] wherein the method is further defined as strengthening the tissue, stabilizing the tissue shape, changing the shape of the tissue, or a combination thereof.

Some embodiments herein are the method of paragraph [0024] or [0025] wherein the tissue is an ocular tissue.

Some embodiments herein are the method of paragraphs [0024] to [0026] wherein the ocular tissue includes at least a portion of a cornea and/or a sclera.

Some embodiments herein are the method of paragraphs [0024] to [0027] wherein the ocular tissue includes at least a portion of a lamina cribrosa.

Some embodiments herein are the method of paragraphs [0024] to [0028] wherein the tissue includes at least a portion of the cornea, the method is performed substantially concurrently with a corneal operation and the photoinitiator is provided in a therapeutically effective amount which directly reduces the risk of a post operative corneal deformation condition.

Some embodiments herein are the method of paragraphs [0024] to [0029] wherein
  a) the subject has or is at risk of developing an ocular deformation condition comprising one or more of keratoconus, post-laser-assisted in situ keratomileusis (LASIK) ectasia, post-photorefractive keratectomy (PRK) ectasia, post-infection ectasia, peripheral ectasia, rheumatoid condition of the cornea, degenerative myopia, regular myopia, scleral staphyloma, ocular hypertension glaucoma, or low tension glaucoma,
  b) the photoinitiator is provided in a therapeutically effective amount which directly treats or directly reduces the risk of the ocular deformation condition, and
  c) the visible light irradiation occurs over a period of 30 minutes or less.

Some embodiments herein are the method of paragraphs [0024] to [0030] wherein the subject has corneal ectasia.

Some embodiments herein are the method of paragraphs [0024] to [0031], wherein the subject has keratoconus.

Some embodiments herein are the method of paragraphs [0024] to [0032] wherein the individual has degenerative myopia.

Some embodiments herein are the method of paragraphs [0024] to [0033], wherein the photoinitiator compound comprises a photoinitiator, a PEG-photoinitiator, or a combination thereof, the photoinitiator having the Formula I:

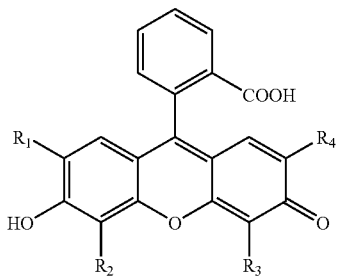

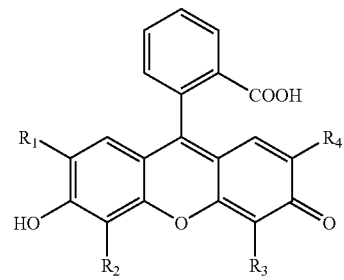

wherein $R_1$, $R_2$, $R_3$, and $R_4$ are each independently, H, halogen, or $NO_2$ and pharmaceutical salts thereof.

Some embodiments herein are the method of paragraph [0034] wherein $R_1$, $R_2$, $R_3$, $R_4$ are each independently H, Br, or $NO_2$.

Some embodiments herein are the method of paragraphs [0024] to [0035] wherein the photoinitiator compound comprises Eosin Y, Eosin B or fluorescein.

Some embodiments herein are the method of paragraphs [0024] to [0036] wherein the providing step is further defined as providing the photoinitiator topically or by injection.

Some embodiments herein are a method of treating or reducing the risk of an ocular deformation condition in a subject comprising the steps of:

a) providing a photoinitiator compound in a therapeutically effective amount to an ocular tissue of the subject; and b) activating the photoinitiator compound by a light irradiation of the tissue, whereby the photoinitiator compound directly treats or reduces the risk of the ocular deformation condition.

Some embodiments herein are the method of paragraph [0038] wherein the photoinitiator is provided to treat an ocular deformation condition and the therapeutically effective amount of the photoinitiator treats a symptom of the ocular deformation condition by strengthening the ocular tissue, stabilizing the ocular tissue shape, changing the shape of the ocular tissue, or a combination thereof.

Some embodiments herein are the method of paragraphs [0038] or [0039] wherein the ocular tissue includes at least a portion of a lamina cribrosa, a cornea and/or a sclera.

Some embodiments herein are the method of paragraphs [0038] to [0040] wherein the subject has or is at risk of having an ocular deformation condition comprising one or more of keratoconus, post-laser-assisted in situ keratomileusis (LASIK) ectasia, post-photorefractive keratectomy (PRK) ectasia, post-infection ectasia, peripheral ectasia, rheumatoid condition of the cornea, degenerative myopia, regular myopia or scleral staphyloma, ocular hypertension glaucoma, or low tension glaucoma.

Some embodiments herein are the method of paragraphs [0038] to [0041] wherein the ocular deformation condition is degenerative myopia.

Some embodiments herein are the method of paragraphs [0038] to [0042] wherein the ocular deformation condition is keratoconus.

Some embodiments herein are the method of paragraphs [0038] to [0043] wherein the photoinitiator compound comprises a compound defined by Formula I:

wherein $R_1$, $R_2$, $R_3$, and $R_4$ are each independently, H, halogen, or $NO_2$ and pharmaceutical salts thereof.

Some embodiments herein are the method of paragraphs [0038] to [0044] wherein the photoinitiator compound comprises a polyethylene glycol derivative of a compound represented by Formula I.

Some embodiments herein are the method of paragraphs [0038] to [0045] wherein the photoinitiator compound is capable of directly treating the ocular deformation condition upon illumination of the photoinitiator compound for 30 minutes or less using light comprising a wavelength of 500±50 nm at an illumination intensity of from 1-100 mW/cm².

Some embodiments herein are the method of paragraphs [0038] to [0046] wherein the photoinitiator is provided by topical administration.

Some embodiments herein are the method of paragraphs [0038] to [0047] wherein the photoinitiator is provided by injection.

Some embodiments herein are the method of paragraphs [0038] to [0048] wherein the ocular tissue includes at least a portion of the cornea, the method is performed substantially concurrently with a corneal operation and the photoinitiator is provided in a therapeutically effective amount which directly reduces the risk of a post operative corneal deformation condition.

Some embodiments herein are a use of a photoinitiator compound for manufacturing a medicament for a direct treatment or prevention of an ocular deformation condition by the photoinitiator compound.

Some embodiments herein are a photoinitiator compound for use as a medicament for directly treating or reducing the risk of an ocular deformation condition.

Some embodiments herein are the use according to any of the preceding paragraphs [0050] to [0051] wherein the direct treatment, prevention or reduction of the risk of the ocular deformation condition comprises an increased modulus of an ocular tissue.

Some embodiments herein are the use according to paragraph [0052] wherein the ocular tissue includes at least a portion of the sclera and/or the cornea and optionally includes the entirety of the sclera and/or the cornea.

Some embodiments herein are the use according to any of the preceding paragraphs [0050] to [0053] wherein the ocular deformation condition is selected from the group consisting of keratoconus, post-laser-assisted in situ keratomileusis (LASIK) ectasia, post-photorefractive keratectomy (PRK) ectasia, post-infection ectasia, peripheral ectasia, rheumatoid condition of the cornea, degenerative myopia, regular myopia, scleral staphyloma, ocular hypertension glaucoma, low tension glaucoma and combinations thereof.

Some embodiments herein are the use according to any of the preceding paragraphs [0050] to [0054] wherein the ocular deformation condition is degenerative myopia.

Some embodiments herein are the use according to any of the preceding paragraphs [0050] to [0055] wherein the ocular deformation condition is keratoconus.

Some embodiments herein are the use according to any of the preceding paragraphs [0050] to [0056] wherein the photoinitiator compound comprises a compound having the Formula I:

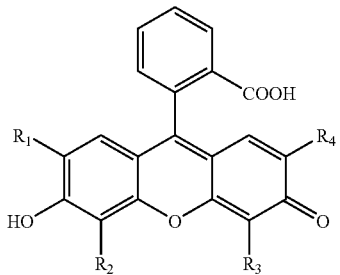

wherein $R_1$, $R_2$, $R_3$, and $R_4$ are each independently, H, halogen, or $NO_2$ and pharmaceutical salts thereof.

Some embodiments herein are the use according to the preceding paragraph [0057] wherein $R_1$, $R_2$, $R_3$, $R_4$ are each independently H, Br, or $NO_2$.

Some embodiments herein are the use according to any of the preceding paragraphs [0050] to [0058], wherein the photoinitiator compound comprises Eosin Y, Eosin B or fluorescein.

Some embodiments herein are the use according to any of the preceding paragraphs [0050] to [0059] wherein the photoinitiator compound comprises a polyethylene glycol derivative thereof.

Some embodiments herein are the use according to any of the preceding paragraphs [0050] to [0060] wherein the photoinitiator compound is capable of directly treating or reducing the risk of the ocular deformation condition upon illumination of the photoinitiator compound within an ocular tissue for 30 minutes or less using visible light.

Some embodiments herein are the use according to any of the preceding paragraphs [0050] to [0061] wherein the medicament is for topical administration.

Some embodiments herein are the use according to any of the preceding paragraphs [0050] to [0062] wherein the medicament is for administration by injection.

Some embodiments herein are the use of a photoinitiator compound for manufacturing a medicament for directly altering a mechanical and/or chemical property of a tissue.

Some embodiments herein are the use according to paragraph [0064] wherein the tissue is an ocular tissue and the direct alteration of the mechanical and/or chemical property of the ocular tissue comprises an increased modulus of the ocular tissue.

Some embodiments herein are the use according to paragraph [0065] wherein the ocular tissue includes at least a portion of the sclera, the lamina cribrosa, or the cornea and optionally includes the entirety of the sclera and/or the cornea and/or the lamina cribrosa.

Some embodiments herein are the use according to paragraphs [0065] to wherein the ocular tissue is in an eye of a subject having or at risk of having a condition selected from the group consisting of keratoconus, post-laser-assisted in situ keratomileusis (LASIK) ectasia, post-photorefractive keratectomy (PRK) ectasia, post-infection ectasia, peripheral ectasia, rheumatoid condition of the cornea, degenerative myopia, regular myopia, scleral staphyloma, ocular hypertension glaucoma, low tension glaucoma and combinations thereof.

Some embodiments herein are the use according to paragraph [0067] wherein the ocular deformation condition is degenerative myopia.

Some embodiments herein are the use according to paragraph [0067] wherein the ocular deformation condition is keratoconus.

Some embodiments herein are the use according to paragraphs [0064] to wherein the photoinitiator compound comprises a compound having the Formula I:

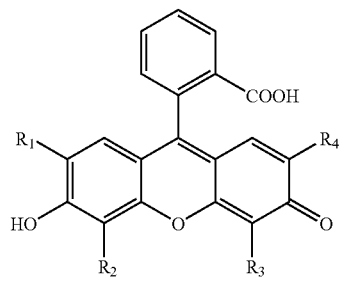

wherein $R_1$, $R_2$, $R_3$, and $R_4$ are each independently, H, halogen, or $NO_2$ and pharmaceutical salts thereof.

Some embodiments herein are the use according to paragraph [0070] wherein $R_1$, $R_2$, $R_3$, $R_4$ are each independently H, Br, or $NO_2$.

Some embodiments herein are the use according to paragraphs [0064] to wherein the photoinitiator compound comprises Eosin Y, Eosin B or fluorescein.

Some embodiments herein are the use according to paragraphs [0064] to wherein the photoinitiator compound comprises a polyethylene glycol derivative of a compound of Formula I.

Some embodiments herein are the use according to paragraphs [0064] to wherein the photoinitiator compound is capable of directly treating or reducing the risk of the ocular deformation condition upon illumination for 30 minutes or less, using light comprising a wavelength of 500±50 nm, and at an illumination intensity of from 1-100 $mW/cm^2$.

Some embodiments herein are the use according to paragraphs [0064] to wherein the medicament is for topical administration.

Some embodiments herein are the use according to paragraphs [0064] to wherein the medicament is for administration by injection.

Some embodiments herein are the use according to paragraphs [0064] to wherein the direct treatment, direct reduction of risk of or direct prevention of an ocular deformation condition comprises an illumination of the medicament at a wavelength of 500±50 nm at an illumination intensity of from 1-100 $mW/cm^2$.

Some embodiments herein are the methods of paragraphs [0024] to [0049] wherein the duration of time between the providing and activating steps is between about 1 and 120 minutes; between about 1 and 60 minutes; between about 60 and 120 minutes; between about 1 and 30 minutes; between about 30 and 60 minutes; between about 60 and 90 minutes; between about 90 and 120 minutes; between about 5 minutes and about 10 minutes; or between about 1 minute and 5 minutes.

Some embodiments herein are the methods of paragraphs [0024] to [0049], or [0078] wherein the method is repeated one, two, three, four, five or more times.

Some embodiments herein are the methods of paragraphs [0024] to [0049], or [0078] to [0079] wherein the activating step is no longer than about 30 minutes; no longer than about 20 minutes; no longer than about 10 minutes; no longer than about 5 minutes; no longer than about 1 minute; or no longer than about 30 seconds.

Some embodiments herein are the use according to paragraphs [0050] to wherein the medicament is for provision to a tissue followed by photo activation and the duration of time between the providing and activating is between about 1 and 120 minutes; between about 1 and 60 minutes; between about 60 and 120 minutes; between about 1 and 30 minutes; between about 30 and 60 minutes; between about 60 and 90 minutes; between about 90 and 120 minutes; between about 5 minutes and about 10 minutes; or between about 1 minute and 5 minutes.

Some embodiments herein are the use according to paragraphs [0050] to [0077], or [0081] wherein the medicament is for activation with light for no longer than about 30 minutes; no longer than about 20 minutes; no longer than about 10 minutes; no longer than about 5 minutes; no longer than about 1 minute; or no longer than about 30 seconds.

The foregoing has outlined some of the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIGS. 7A and 7B show typical results from ocular inflation studies with Eosin Y on eyes with their corneal epithelium intact (measurements in digital image pixels).

FIGS. 8A and 8B show typical results from ocular inflation studies with Eosin Y on eyes with their corneal epithelium removed prior to addition of Eosin Y (measurements in digital image pixels).

FIG. 9 shows an exemplary chemical synthesis pathway for creating a PEG derivative of Eosin Y.

FIG. 11B. Slit lamp images showing A) the full thickness of an Eosin Y treated cornea (Filter 2 out, FIG. 11A), B) isolated fluorescence within the stroma (Filter 2 in, as shown in FIG. 11A); C) and the automated fluorescence intensity analysis using the MATLAB® software.

DETAILED DESCRIPTION OF THE INVENTION

Figure 1:
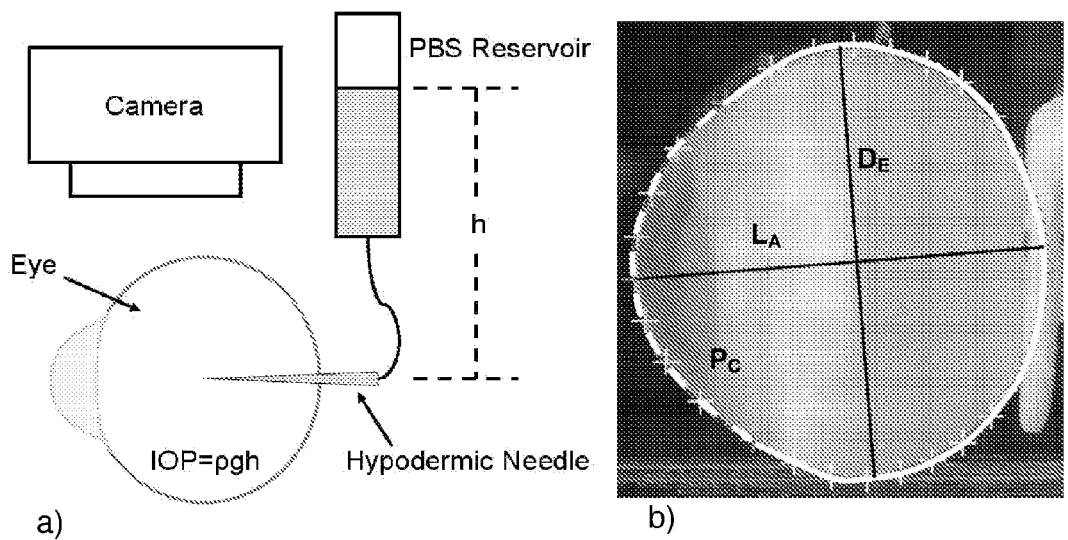
FIG. 1 is an exemplary apparatus to monitor eye shape changes during application of elevated pressure.

In keeping with long-standing patent law convention, the words "a" and "an" when used in the present specification in concert with the word comprising, including the claims, denote "one or more." The words "comprising" and "comprises" indicates an open claim or claim limitation. Some embodiments of the invention may consist of or consist essentially of one or more elements, method steps, and/or methods of the invention. It is contemplated that any method or composition described herein can be implemented with respect to any other method or composition described herein.

DEFINITIONS

The term "cornea" as used herein refers to the transparent, dome-shaped covering of the front of the eye. It normally functions as a refracting surface, providing more than half of the focusing power for the eye. There are no blood vessels in the cornea, so it is usually clear and has a shiny surface. It is comprised of 5 layers: epithelium, Bowman's membrane, stroma, Descemet's membrane and the endothelium. The cornea also houses more nerve endings than anywhere else in the body.

The terms "crosslink" or "crosslinking" as used herein refers to formation of a covalent bond between two molecules. For example, a collagen molecule may be crosslinked to other collagen molecules to form a network of interlinked collagen molecules held together by a covalent linkages.

The term "ectasia" as used herein refers to dilatation or distension of a hollow organ. In specific embodiments of the invention, the term refers to bulging of an ocular tissue, such as the cornea. In further specific embodiments, the ectasia is surgically-induced, although in alternative embodiments it is not due to surgery and may be due to the exemplary medical condition keratoconus. In particular cases, ectasia is the result of Laser-Assisted in Situ Keratomileusis (LASIK).

The term "keratoconus" as used herein refers to a medical condition in which the cornea, which is normally round, develops a cone-like shape from thinning and/or bulging of the cornea. The shape of the cone causes irregular refraction of light as it enters the eye on its way to the light-sensitive retina, which results in distorted vision. Keratoconus is a progressive disease and can occur in one or both of the eyes.

The term "sclera" as used herein refers to the tough, opaque (usually white), outer fibrous coat of the eye, continuous with cornea anteriorly and the optic nerve posteriorly. It comprises collagen and elastic fibers and is often referred to as "the white of the eye." Multiple muscles connect to the sclera around the eye and control its movements. At the very back of the eye, the optic nerve is attached to the sclera. The term "sclera" as used herein refers to the outer fibrous coat of the eye, continuous with cornea anterioly and the optic nerve posteriorly.

The term "mechanical and/or chemical property of a tissue" as used herein refers to the biophysical properties of the tissue. Examples of a mechanical property include but are not limited to tensile strength, compression strength, flexural strength, modulus, elongation and toughness (stress-strain). Examples of a chemical property include but are not limited to the nature of chemical bonds of the tissue components (e.g. collagen versus crosslinked collagen), amount of water of hydration of the tissue is capable of retaining, the biodegradation or turnover rate of tissue constituents.

The term "changing the shape of the tissue" refers to combining photoinitiator treatment with a means for altering the shape of a tissue to stabilize the tissue in the altered shape. For example, a cornea may be temporarily reshaped by means of a plastic mould designed to induce a shape in the cornea which would improve the vision of any eye. By combining such shaping means with treatment with a therapeutically effective amount of photoinitiator, the corrective shape of the tissue can be maintained after removal of the shape altering means by illumination while the shaping means is in place.

The term "therapeutically effective amount" refers to the amount required to directly cause alteration of one or more mechanical or chemical properties of a tissue to a sufficient degree to treat a symptom of an ocular deformation condition.

The term "ocular deformation condition" as used herein refers to a disease or physical change in the eye of a subject which results in a change in the dimension of one or more structures of the eye. In some embodiments, this change in dimension causes a change in vision. Specific examples of ocular deformation conditions include corneal deformation conditions such as keratoconus (including posterior keratoconous); the post operative corneal deformation conditions of post-laser-assisted in situ keratomileusis (LASIK) ectasia and post-photorefractive keratectomy (PRK) ectasia; post-infection ectasia, peripheral ectasia, rheumatoid condition of the cornea, degenerative myopia, regular myopia, scleral staphyloma, and glaucoma (including ocular hypertension glaucoma and low tension glaucoma).

The term "photoinitiator" as used herein refers to a compound capable of converting absorbed light energy, generally UV or visible light, into chemical energy in the form of initiating species, e.g., free radicals or cations. Based on the mechanism by which initiating radicals are formed, photoinitiators are generally divided into two classes: Type I photoinitiators undergo a unimolecular bond cleavage upon irradiation to yield free radicals; Type II photoinitiators undergo a bimolecular reaction where the excited state of the photoinitiator interacts with a second molecule (a coinitiator) to generate free radicals. UV photoinitiators of both Type I and Type II are known whereas visible light photoinitiators generally belong to the Type II class. A skilled artisan recognizes that the choice of photoinitiator dictates the type of light source employed, and that different photoinitiators are active at different wavelengths and with different efficiencies. In particular, the spatial resolution with which the photoinitiator can be excited is dependent on whether the photoinitiator is excited via single-photon or multi-photon excitation. The photoinitiators may be in particular embodiments water soluble, inhibited by oxygen, and are preferably biocompatible. Diffusion of the photoinitiators into the sclera and/or cornea is governed by the size of the compounds, and the hydrophilic and/or hydrophobic interactions of the photoinitiators with the tissue(s). Desired diffusion rates will be fast in order to minimize treatment time. High efficiency photoinitiators are desirable because irradiation energy, irradiation time, and photoinitiator concentration are minimized. Preferably, oxygen acts as an inhibitor to lower the efficiency of the photoinitiator. This inhibition will provide a method of protecting oxygen carrying blood vessels from any deleterious effects of photoinitiator activation with light. In specific embodiments, photoinitiators are employed that are water soluble, non-toxic, and sensitive to the amount of oxygen concentration. Exemplary photoinitiators include compounds of Formula I herein, IRGACURE® 2959, and those photoinitiators disclosed in FIGs. 10B, 10C and 10E of U.S. Published Application No. 20050271590.

The term "modulus" as used herein refers to a constant or coefficient that represents, such as numerically, for example, the degree to which a substance or body possesses a mechanical property (such as strength or elasticity, for example). A skilled artisan recognizes that the ranges of modulus depend on the exact method of measurement, the specific type of modulus being measured, the material being measured, and in the case of the sclera, the condition of the tissue (as in age or health) and the tissue's location on the ocular globe. Examples of moduli include Young's modulus (also known as the Young modulus, modulus of elasticity, elastic modulus or tensile modulus), the bulk modulus (K) and the shear modulus (G, or sometimes S or µ) also referred to as the modulus of rigidity.

The term "ocular tissue" as used herein refers to a discrete tissue type found in or associated with an eye. In some embodiments, the ocular tissue is a structural tissue which establishes and/or maintains the shape of an eye. In other embodiment, the ocular tissue contributes to the vision of an eye. Specific examples of ocular tissues include the sclera, lamina cribosa, and the cornea.

The terms "direct treatment," "directly treating," "directly reducing the risk of" and the like refer to photoinitiator based therapy where the photoinitiator directly interacts with tissue components to cause a change in tissue properties. Direct treatment with a photoinitiator is distinguished from indirect photoinitiator treatment wherein a photoinitiator interacts with one or more other chemical agents to change the structure of the other chemical agents and the changes in the other chemical agent cause a change in tissue properties. An example of indirect photoinitiator treatments is found in U.S. Published Application No. 20050271590, where Eosin Y/TEOA is used as a photoinitiator of PEGDM crosslinking for reinforcement of scleral tissues. The terms "direct treatment," "directly treating" and the like as used herein additionally refer to the amelioration of at least one symptom of an disease or condition such as an ocular deformation condition. By way of example, in myopia, symptoms include scleral stretching, scleral thinning, or scleral weakening. Furthermore, a skilled artisan recognizes that the treatment does not need to improve vision, such as improving it to its fullest extent. In particular aspects, the terms refer to preventing the progression or slowing the progression of an ocular deformation condition such as degenerative myopia or keratoconous. In a specific embodiment, the vision stabilizes.

The terms "polyethylene glycol" and "PEG" as used herein refers to a compound comprising more than one partial or whole poly(ethylene-glycol) backbone monomer of ethylene-glycol with or without differing endgroups and also comprising some or no other monomers such as, for example, dimethyl siloxane, methyl methacrylate, lysine, arginine, chondroitin sulfate, keratin sulfate, etc. In specific embodiments, it is defined as an oligomer or a polymer comprising the repeated units of ethylene glycol (—$OCH_2CH_2$—).

The term "myopia" as used herein, which may also be referred to as near-sightedness, refers to the ability to clearly see objects up close but not those at a distance. The present invention is suitable for all forms and degrees of myopia. In specific embodiments, myopia is pathologic and is diagnosed when eyeball elongation is associated with thinning of ocular tissues in the posterior portion of the globe. High myopia is defined as greater than 8 diopters.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66: 1 19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

"Performed substantially concurrently with" as used herein means application of a method disclosed herein within a period of time that is sufficiently close in time to a medical procedure to prevent or reduce the risk of a potential complication of the procedure. A medical professional performing the procedure will be well informed by the guidance and examples herein and thereby capable of determining the appropriate timing. In some embodiments, the application of a method disclosed herein is after a medical procedure, and in specific embodiments up to 5, 10, 15, 20, 25, 30, 35, 40, 45, 50, 60, 75, 90 or 120 minutes or more after a medical procedure.

"Corneal operation" as used herein means any medical procedure which involves reshaping or surgically altering a cornea such as laser-assisted in situ keratomileusis (LASIK) or photorefractive keratectomy (PRK).

"Visible light" as used herein refers to electromagnetic radiation having a wavelength of from about 400 nm to about 780 nm. In some embodiments, the visible light is electromagnetic radiation having a wavelength of a) from about 400 nm-about 750 nm, b) from about 400 nm-about 700 nm or c) from about 450 nm to about 700 nm.

Embodiments of the Present Invention

In embodiments of the present invention, there are methods and compositions concerning altering one or more mechanical and/or chemical properties of a tissue in the body of an individual. In certain cases, the tissue is an ocular tissue, and in specific embodiments, the ocular tissue is cornea or sclera. In a particular yet exemplary embodiment, the present invention concerns altering one or more mechanical and/or chemical properties of the cornea, such as for an individual with keratoconus.

In specific embodiments, to prevent loss of vision due to keratoconus, the present inventors have devised a minimally invasive, safe and rapid method to introduce therapeutic crosslinking in, for example the cornea, lamina cribosa or sclera. While slowing the progression of keratoconus is one specific embodiment of the invention, the invention also provides the ability to crosslink or polymerize custom molecules to other parts of the eye, such as those within the cornea, sclera and lamina cribrosa, for example. The present invention applies to a diversity of conditions in which the shape of a tissue is unstable (cannot maintain its normal shape) and/or requires re-shaping. Examples relevant to vision include keratoconus, posterior keratoconus, post-laser-assisted in situ keratomileusis (LASIK) ectasias, post-photorefractive keratectomy (PRK) ectasias, post-infection ectasias, peripheral ectasias (such as pellucid marginal corneal degeneration), rheumatoid conditions of the cornea, degenerative myopia, regular myopia, scleral staphylomas, glaucoma and normal tension glaucoma.

The inventors have developed a clinically relevant combination of exemplary topically applied or injected photoinitiator and visible light irradiation to generate sufficient crosslinking to arrest progression of keratoconus. Using insight into partitioning and transport of molecules into the cornea, one can modify or generate a new molecule that penetrates the epithelium without epithelial toxicity. Photoinitiators that permeate the cornea adequately diffuse into the corneal stroma in sufficient concentration to achieve clinical effect with subsequent photoactivation. Photoinitiators that permeate the corneal epithelium are excellent compounds for permeating other tissues, such as the sclera. Some photoinitiators of interest do not permeate the corneal epithelium and can be delivered into the stroma by injection. This allows one to treat without removing the corneal epithelium. Next, the inventors show that one can treat tissues without exposing tissues to potentially damaging UV light. Treatments are provided that are activated by visible light, and the risks of retinal and corneal damage caused by uv irradiation are avoided. In addition, one is able to localize crosslinking using irradiation patterns to avoid crosslinking in untargeted tissues. The interplay of photoinitiator concentration and light intensity govern the exposure time required to effect the necessary degree of crosslinking for a patient. Results indicate that irradiation times less than 5 minutes are possible. This will shorten the treatment time from 30 minutes using riboflavin and uv light to about 5 minutes and vastly simplify the procedure for treated individuals, such as patients, and health care providers, such as surgeons. Further control of light activation (including activation at a selected depth within a tissue, such as below the epithelium and above the endothelium of the cornea) can be achieved by extending the present invention to two-photon or multiphoton activation. Activation using highly-convergent infrared light further reduces risk of irradiation-induced toxicity.

Light Activation

In certain aspects of the invention, one or more photoinitiators are provided to one or more tissues in the body and are activated with light. Although in certain aspects the light may be of any kind, in particular embodiments it is visible light, ultraviolet light, or infrared light. The activation may be two-photon or multiphoton activation. In further particular embodiments, visible light irradiation is employed.

The duration of the exposure to light may be of any suitable kind so long as the target molecule(s) are activated from the light. In particular aspects, the light exposure is continuous, although in some cases it is intermittent. In additional aspects, the light is applied for about one or more seconds, one or more minutes, or one or more hours. In specific cases, the light is applied for at least about one minute, at least about two minutes, at least about three minutes, at least about four minutes, at least about five minutes, at least about six minutes, at least about seven minutes, at least about eight minutes, at least about nine minutes, at least about ten minutes, at least about eleven minutes, at least about twelve minutes, at least about thirteen minutes, at least about fourteen minutes, at least about fifteen minutes, and so forth. In other cases, the light is applied no more than about thirty minutes, no more than about twenty five minutes, no more than about twenty minutes, no more than about fifteen minutes, no more than about ten minutes, no more than about nine minutes, no more than about eight minutes, no more than about seven minutes, no more than about six minutes, no more than about five minutes, no more than about four minutes, no more than about three minutes, no more than about two minutes, or no more than about one minute.

Exemplary light sources for visible light irradiation include lamps (e.g. a Mercury Xenon Arc Lamp, optionally filtered to emit a subset of light wavelengths), lasers, and light-emitting diodes (LED). Light is generally used at an intensity of 1-100 mW/cm$^2$ with the particular light intensity dependent on, among other factors, the tissues and photoinitiators compound(s) involved. One of skill in the art will readily be able to adjust light intensity and time of illumination for a particular application.

Photoinitiators

A. Exemplary Photoinitiators

In certain embodiments of the present invention, one or more photoinitiators are provided to a tissue of an individual so that the mechanical and/or chemical properties of the tissue are affected. In specific embodiments, one or more photoinitiators are provided to a tissue of an individual so that the tissue is strengthened and/or shape of tissue is altered. In certain aspects, a therapeutically effective amount of the photoinitiator(s) is employed, which refers to the amount required to directly cause alteration of one or more mechanical or chemical properties of a tissue to a sufficient degree to treat a symptom of an ocular deformation condition.

Any suitable photoinitiator may be used in the invention so long as it is photoactivatable and upon photoactivation it directly affects at least one mechanical and/or chemical properties of a desired tissue. In some embodiments, the photoinitiator is a Type II photoinitiator. In other embodiments, the photoinitiator is a visible light Type II photoinitiator.

In certain other embodiments, the photoinitiator is a compound represented by Formula I and pharmaceutical salts of Formula I:

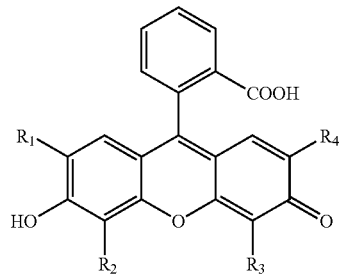

Formula I wherein $R_1$, $R_2$, $R_3$, and $R_4$ are each independently H, halogen, or $NO_2$.

In certain embodiments, $R_1$, $R_2$, $R_3$, $R_4$ are each independently, H, Br, F, or $NO_2$. In other embodiments, $R_2$, $R_3$, $R_4$ are each independently, H, Br, or $NO_2$. In still other embodiments, $R_1$, $R_2$, $R_3$, $R_4$ are each hydrogen (this compound is also known as fluorescein). In other embodiments, $R_1$ and $R_4$ are each $NO_2$ and $R_2$ and $R_3$ are each Br (this compound is also known as Eosin B). In still other embodiments, $R_1$, $R_2$, $R_3$, $R_4$ are each Br (this compound is also known as Eosin Y).

An exemplary compound of the invention, Eosin Y, will be used to described the present invention in greater detail.

Eosin Y is most commonly known as a water soluble xanthene dye and is a common stain for collagen. Eosin Y is a Type II photoinitiator that is typically used in combination with triethanolamine (TEOA). However, as with other Type II photoinitiators, any suitable co-initiator can be used. Having an absorption peak around 514 nm, Eosin Y is activated efficiently by low-toxicity, visible (green) light.

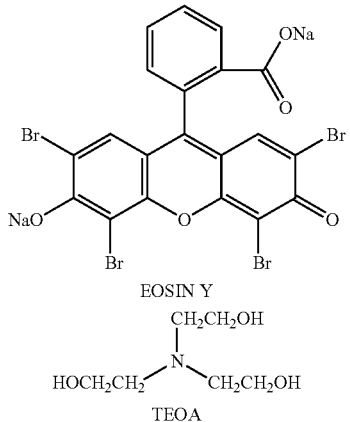

Notably, Eosin Y itself has a well established track record of biocompatibility in a range of applications as shown by Table 1.

TABLE 1

Literature demonstrating biocompatibility of Eosin Y photoinitiator systems.

| Authors | Application |
|---|---|
| Nakayama et. al. | Hemostasis of Liver Tissue |
| Orban et. al. | Cardiovascular Applications |
| Cruise et. al., Pathak et. al., Desmangles et. al. | Islet Cell Encapsulation/ Microencapsulation |
| Elisseeff et. al. | Transdermal Polymerization |
| Luman et. al. Carnahan et. al. | Close linear corneal incisions, Secure Lasik flaps |
| Alleyne et. al. | Dural Sealant in Canine Craniotomy (FocalSeal) |
| West et. al. | Thrombosis Inhibition |

In particular embodiments, the photoinitiator is combined with one or more labels, so that the location and/or amount of the photoinitiator can be monitored once it is delivered to the a subject. Exemplary labels include a fluorescent labels which optionally may be selected to fluoresce at wavelengths of light which do not substantially activate the photoinitiator.

Although permeability measurements of almost 150 different compounds exist, there are no reliable predictive formulas for diffusion of chemicals across the cornea (Prausnitz and Noonan, 1998). Trends show that increased lipophilicity can assist transport across the epithelial barrier (Tangliu et al., 1994; Sasaki et al., 1995). Also, removing charges from pharmaceuticals may improve permeability. In vitro measurements correlate well with in vivo results for epithelial permeation, provided the tissue specimen has its epithelium intact. In some embodiments, one method of improving penetration of Formula I compounds through the epithelium is to decrease its charge by making carboxylate derivatives thereof. One such modification is to add a short PEG to the carboxylate site. For example, one can prepare PEG-grafted Eosin Y (PEG-EY) by tosylating PEG-OH and grafting it to carboxylic acid site. For example, three lengths of commercially available but exemplary PEG-OH can be used: ~200, 400 and 800 g/mol.

The stroma, the thickest layer of the cornea, comprises a complex arrangement of collagen fibrils, glycosaminoglycans and proteoglycans. Insight into the molecular basis of corneal stabilization from the study of model systems (collagen networks, polylysine, polyarginine, polycysteine, hyaluronic acid, dermatan sulfate, keratan sulfate, chondroitan sulfate, or heparin sulfate) allows variations of Eosin Y or new photoinitiator compounds to target specific interactions that increase efficacy.

B. Delivery of Photoinitiator

In some embodiments, the photoinitiator(s) may be delivered by any suitable manner and using any suitable regimen, so long as a therapeutically effective amount is employed. In particular embodiments, the photoinitiator(s) is delivered topically, by injection, by contacts (including sustained release contacts), by a sponge soaked in photoinitiator, and so forth. Eye drops may be employed, and in some cases the photoinitiator(s) is lyophilized. Photoinitiator(s) may also be delivered to a cornea through injection into the stroma with fine-gauge needles; this stromally injected photoinitiator can diffuse into stromal lamellae.

The time between photoinitiator delivery and irradiation may be adjusted for individual patients and may depend on a variety of factors, including the diffusion rate of the photoinitiator(s) into the target tissue and the stability of the photoinitiator(s) under the conditions of administration (e.g. ambient light intensity). The photoinitiator(s) may be provided to the individual, and then following an amount of time to ensure that the photoinitiator(s) has reached a particular location and/or sufficient level, for example, the irradiation may then be applied. For example, the photoinitiator(s) may be monitored with slit lamps and/or confocal microscopes while the photoinitiator(s) reaches a certain depth in a particular tissue, and then the photoinitiator(s) is activated with light. In a particular example, the photoinitiator(s) is monitored while it penetrates the cornea to a certain depth, and then the photoinitiator(s) is activated with light.

The amount of time between photoinitiator delivery and photoactivation of the photoinitiator(s) may be of any suitable duration, although in specific embodiments, the time is on the order of seconds, minutes, or hours. In specific embodiments, the amount of time is about one minute, about two minutes, about three minutes, on up to about 120 minutes. In additional specific embodiments, the duration between photoinitiator delivery and photoactivation of the photoinitiator(s) is no longer than about one minute, about two minutes, about three minutes, about 5 minutes, about 10 minutes, about 20 minutes, on up to about 120 minutes.

C. Tissue Irradiation

Illumination of photoinitiator treated tissues may be accomplished by a number of devices and techniques. Slit lamp delivery systems, fiber optic light systems, illumination by an indirect ophthalmoscope delivery system are all examples of illumination devices readily adaptable to the uses and methods disclosed herein. Any suitable device or technique may be used that is capable of delivering the appropriate wavelength(s) of light at an appropriate intensity for a sufficient amount of time, based generally on the specific photoinitiator(s) in use and other parameters disclosed herein.

Treatment of Medical Conditions

In specific aspects of the invention, the methods and compositions may be employed for any medical condition of a subject in need thereof. Although in particular aspects the subject is a human, in further aspects the invention is useful for other mammals, such as a horse, cow, dog, cat, goat, sheep, or pig, for example.

Treatments may be repeated in the individual as needed. For example, a second or more treatment may be applied within days of a previous treatment, within weeks of a previous treatment, or within months of a previous treatment.

A. Ocular Medical Conditions

In embodiments of the invention, there is treatment of an ocular deformation condition. In specific embodiments, the ocular deformation condition comprises keratoconus, posterior keratoconus, post-LASIK ectasias, post-PRK ectasias, post-infection ectasias, peripheral ectasias (such as pellucid marginal corneal degeneration), rheumatoid conditions of the cornea, degenerative myopia, regular myopia and/or scleral staphylomas, glaucoma, normal tension glaucoma, and ocular hypertension. In some embodiments, the methods herein may be used prophylactically to reduce the risk of or prevent an ocular deformation condition including any of the foregoing. In particular embodiments, the methods herein are applied to a cornea concurrently with, or soon after undergoing, a LASIK, PRK or other corneal operation to reduce the risk of a postoperative ecstasia or other corneal deformation conditions which are complications of such operations.

1. Glaucoma

Glaucoma is a leading cause of visual loss throughout the world. In glaucoma, there is progressive loss of retinal ganglion cells associated with cupping of the optic nerve head. Most often, this optic nerve damage occurs at elevated intraocular pressure, greater than 21 mm Hg. Not uncommonly, however, identical optic nerve cupping can be seen at normal intraocular pressures (normal tension glaucoma). Burgoyne and co-workers have shown that intraocular pressure deforms the supporting structure of the optic nerve, the lamina cribrosa as well as the peripapillary sclera. (1. Burgoyne, C F, Downs J C, Bellezza A J et al. The optic nerve head (ONH) as a biomechanical structure: a new paradigm for understanding the role of TOP-related stress and strain in the pathophysiology of glaucomatous optic nerve head damage. Prog Retina Eye Res. 2005; 24:39-73 2. Bellezz A J, Rintalan C J, Thompson H W, et al. Deformation of the lamina cribrosa and anterior scleral canal wall in early experimental glaucoma. Invest Ophthalmol Vis Sci. 2003; 44:623-637 3. Yang J, Downs J C, Girkin C, et al. 3-D histomorphometry of the normal and early glaucomatous monkey optic nerve head: lamina cribrosa and peripapillary scleral position and thickness. Invest Ophthalmol V is Sci. 2007; 48:4597-4607) Intraocular pressure induced posterior deformation and thickening the lamina cribrosa connective tissue is thought to contribute to damage to the axons as they exit the eye with resultant glaucomatous optic atrophy. "From an engineering standpoint, ONH connective tissue susceptibility to damage and permanent deformation should be directly related to its structural stiffness, which is a combination of the structure's geometry (tissue volume and morphology) and material properties (tissue stiffness)." (Yang J, Downs J C, Girkin C, et al. 3-D histomorphometry of the normal and early glaucomatous monkey optic nerve head: lamina cribrosa and peripapillary scleral position and thickness. Invest Ophthalmol V is Sci. 2007; 48:4597-4607) Therefore, if we alter (strengthen) the mechanical properties of the lamina cribrosa and prevent deformation of this tissue in glaucoma, or normal tension glaucoma, we would reduce or even halt the progression of these blinding disorders. Furthermore, in patients at risk for glaucoma, those with ocular hypertension (elevated intraocular pressure without optic nerve head damage), similar strengthening of the connective tissue in the lamina cribrosa and/or peripapillary sclera would prevent or reduce the risk of glaucoma or rate of development of glaucoma.

To selectively treat the lamina and/or the adjacent peripapillary sclera to increase resistance to pressure induced deformation, photoinitiator could be injected introcularly and/or periocularly prior to irradiation. Irradiation could then be applied through the pupil of the eye and directed at the lamina cribrosa and/or peripapillary sclera. Alternatively, irradiation could be applied from a subtenons approach using a fiberoptic probe. Multiphoton irradiation might be particularly useful is controlling activation of the photoinitiator selectively within the target tissue (s), the lamaina cribrosa and/or peripapillary sclera. If the supporting tissue of the optic nerve were thus stabilized, glaucomatous atrophy of the optic nerve could be prevented or slowed.

B. Non-Ocular Medical Conditions

In embodiments of the present invention, the tissue treated comprises a portion of a blood vessel. For example, a blood vessel wall at risk for an aneurism may be strengthened according to the methods disclosed herein to reduce the risk of an aneurism developing or to strengthen an existing aneurism to reduce the risk of the blood vessel wall rupturing.

In other embodiments, the tissue encompasses a hernia or tissue at risk of herniation. By strengthening the tissue according to the methods herein, the risk of herniation or the risk of increased herniation may be reduced.

In other embodiments, the tissue treated comprises Alveolar structures at risk of degeneration such as in COPD patients. The methods herein strengthen the Alveolar structures to reduce the occurrence and rate of Alveolar degeneration.

In other embodiments, the tissue treated may be damaged heart tissue e.g. subsequent to a myocardial infarction. Damaged heart tissue may be strengthened by the methods herein to improve heart function and/or reduce the rate of loss of heart function. For example, strengthened heart tissue in cases of dilated cardiomyopathy may halt or reduce the rate of loss of cardiac pumping capacity.

Assay of Alteration of a Mechanical and/or Chemical Property of a Tissue

In certain aspects of the invention, the alteration of a mechanical and/or chemical property of a tissue is assayed. A variety of materials testing techniques are available to one of skill in the art. For example, Young's modulus of a tissue may be measured using a TA Instruments AR1000 rheometer (using a cleated parallel plate geometry).

In certain aspects of the invention, the alteration of a tissue is assayed by visibly identifying a shape change in the tissue. For example, the ocular inflation assay described below visually measures the swelling of an eye's structures under increased intraocular pressure.

Other instruments and techniques known in the art to characterize mechanical properties of a tissue may also be employed before and after treatment. These know techniques may be found, for instance, in Ahearne M, Yang Y, Then K Y, Liu K K. An indentation technique to characterize the mechanical and viscoelastic properties of human and porcine corneas. Ann Biomed Eng. 2007 September; 35(9):1608-16; and Gatinel D, Chaabouni S, Adam P A, Munck J, Puech M, Hoang-Xuan T. Corneal hysteresis, resistance factor, topography, and pachymetry after corneal lamellar flap. J Refract Surg. 2007 January; 23(1):76-84; and the other relevant references cited herein.

Exemplary Ocular Treatment

An exemplary treatment procedure may be as follows. A topical application of formulated eye drops comprising Eosin Y is given to an individual 1-120 minutes before irradiation. This provides time for the agent(s) to diffuse into the sclera. After about 1-120 minutes, the eye is irradiated with visible light for about 1-5 minutes (1-100 mW/cm$^2$ at a wavelength appropriate to the specific photoinitiator, for example, 500±50 nm for Eosin Y). Ophthalmic-balanced saline solution eye drops can be used to rinse the eye after administration of the photoinitiator and before photoactivation. Suitable modes of clinical implementation of irradiation include having the patient in a supine position and delivering light through an operating microscope or having the patient seated and delivering light using a slit lamp system. One can also use a fiberoptic light source directed at the sclera via a subconjunctival or subtenons approach. Suitable light sources for irradiation include a lamp, a laser or a light-emitting diode, for example. Suitable methods to control the irradiation pattern incident on the tissue include rastering the irradiation beam, using a spatial light modulator, using a digital mirror device, or using a fiber optic coupled to a laser, for example. The treatment stabilizes the current shape of the sclera and halts or slows progressive change associated with, for example, degenerative myopia. When treatment involves the cornea, subjects are monitored for refractive changes using, for example, corneal topographic assessment. If shape change resumes, the treatment may be repeated as often as necessary (for example, at intervals of 3 to 36 months).

The amount of light exposure may also be changed to adjust the degree of crosslinking that is occurring in the tissue. This may be quantified by measuring the decrease in fluorescence intensity of the photoinitiator during the irradiation procedure. Crosslinking in localized areas may be done using light patterns and even activation by multiphoton light sources.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Poly(ethylene-glycol)dimethacrylate (PEGDM) Polymerization Using Eosin Y/TEOA Photoinitiation Following the teachings of U.S. Published Application No. 20050271590, the Inventors Eosin Y/TEOA as an alternative photoinitiator of PEGDM crosslinking for reinforcement of scleral tissues. It was surprisingly discovered that Eosin Y/TEOA was comparably effective in the absence of a target crosslinking chemical (e.g. PEGDM) for enhancing the strength of scleral tissues. It was particularly unexpected that a Type II photoinitiator was capable of strengthening the sclera to a therapeutically useful degree with illumination periods of approximately 30 minutes or less. Without intending to be bound by the theory, it is believed that Eosin Y may sufficiently promote the direct crosslinking of collagen and other scleral components to enhance the strength of scleral tissue directly. While this does not preclude the co-use of crosslinking chemicals such as PEGDM, the results with Eosin Y suggested a simpler formulation was possible using agents already U.S. Food and Drug Administration approved.

Example 2

Dose Response and Mechanical Properties of Treated Tissue

A number of different techniques were used to initially evaluate scleral tissue strengthening including tensile tests, oscillatory shear measurements and the eye expansion assay discussed more fully below.

The ability of initiator with or without crosslinking compounds to strengthen the sclera was initially evaluated using rheometric analysis of tissue sections. Sclera sections (8 mm diameter) were cut from porcine eyes and tested on a TA Instruments AR1000 rheometer (using a cleated parallel plate geometry) to quantify changes in modulus pre- and post-treatment. Two example photoinitiators were selected for initial evaluation. IRGACURE® 2959 (2-hydroxy-1-[4-(2-hydroxyethoxy)phenyl]-2-methyl-1-propanone) and Eosin Y with triethanolamine (Eosin Y/TEOA). IRGACURE® 2959 (I2959) is a UV light activated photoinitiator that has shown low toxicity in cell encapsulation studies. Eosin Y/TEOA was selected as an example photoinitiator responsive to visible light from the group defined by Formula I. The shear modulus of scleral tissue increased with I2959 plus PEGDM treatments, and the magnitude of the change in modulus increased with decreases in oxygen (oxygen inhibits the polymerization). Similar results were achieved using Eosin Y/TEOA plus PEGDM. As discussed above, it was surprisingly found that comparable increases in modulus occurred upon treatment with I2959 or Eosin Y/TEOA alone.

Example 3

Ocular Shape in Inflation Model of Myopia and Keratoconous

Figure 2:
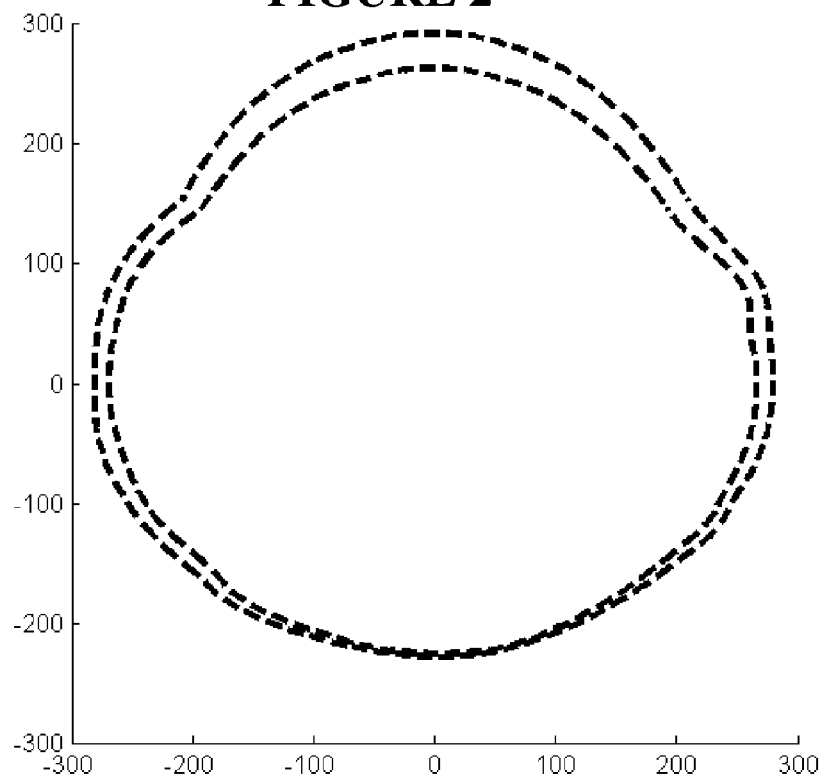
FIG. 2 diagrammatically illustrates ocular inflation due to elevated intraocular pressure (dimensions are in numbers of pixels of a digital image of the eye).
Figure 3:
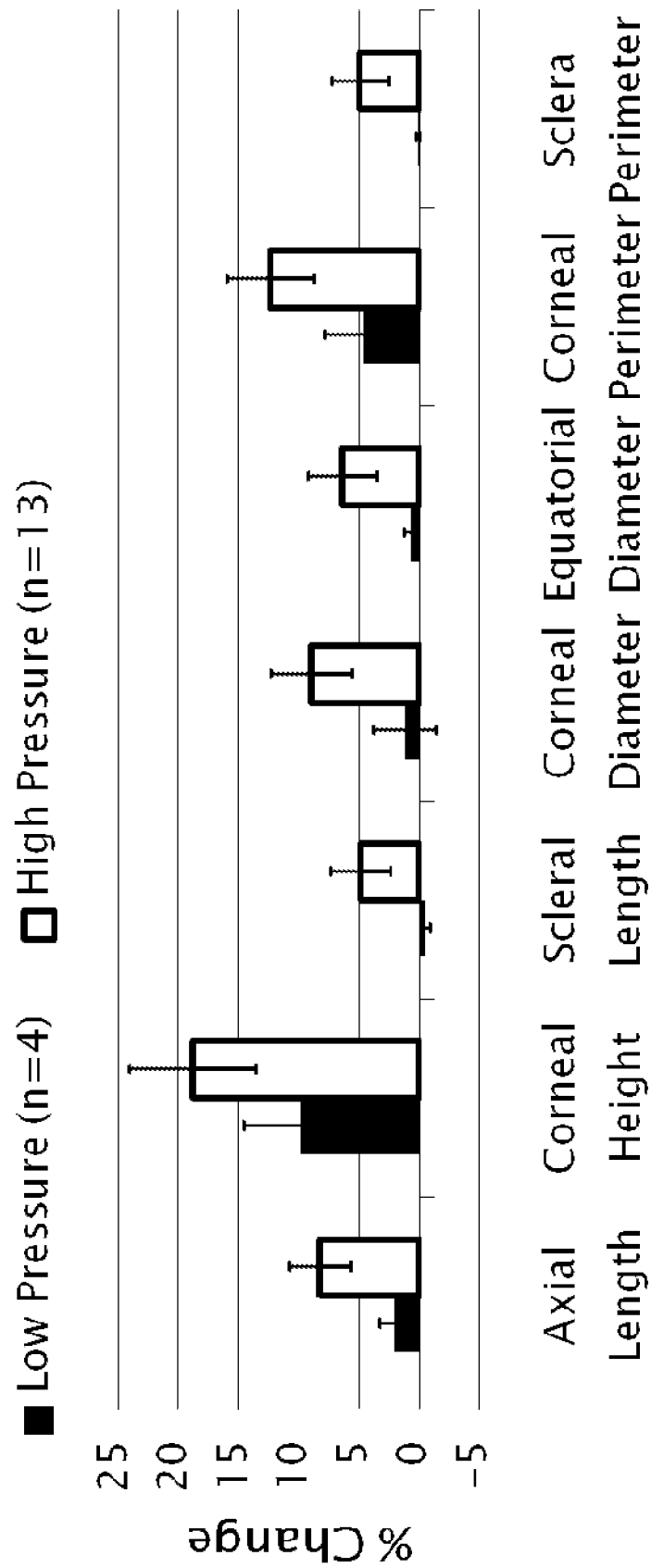
FIG. 3 shows exemplary data from ocular inflation studies where enucleated eyes are uniformly held at an IOP of 22 mmHg for one hour followed by 23 hours of an IOP of 22 mmHg in control eyes and 85 mmHg in test eyes. Ocular inflation studies in all following figures follow this protocol as further detailed in the Examples section.

Stabilization of ocular shape is evaluated in vitro using pairs of enucleated eyes from young (~1-2 weeks) New Zealand White Rabbits, one eye treated and the fellow eye as control. To mimic and accelerate aspects of the loading geometry present in vivo, the intact globes are mechanically tested by imposing an elevated intraocular pressure: a syringe connects the intraocular fluid to an elevated reservoir of Dulbecco's phosphate buffered saline (DPBS) while the exterior of the eye is immersed in DPBS at ambient pressure (FIG. 1). Enucleated eyes from young rabbits provide a model of distensible corneal and scleral tissue: when subjected to elevated intraocular pressure in vitro, the cornea progressively bulges outward and the scleral wall expands (FIGS. 2 and 3).

The size and shape of the globes are simultaneously recorded from two orthogonal perspectives over time. To prepare eyes for the tests, the epithelium is optionally removed from the cornea with a cotton swab, and external fat is removed from the globe. (Note that permeation of the photoinitiator into tissue is examined separately below.) The eyes are then soaked in control (Dulbecco's PBS) or treatment solutions (e.g., 0.029 mM Eosin Y, 90 mM TEOA, in DPBS) for 5 min. After soaking, the eyes are patted dry to remove extra solution from the surface, and then irradiated for 5 min from the front and 5 min from the back with, e.g., 34 mW/cm$^2$ at 500±50 nm for Eosin Y/TEOA. The eye is then loaded in a cell of DPBS while the intraocular pressure (TOP) is maintained at 85 mmHg (~4× normal). Photographs taken every 10 minutes for approximately 24 hours are analyzed to quantify the extension of the cornea and sclera. The foregoing whole eye inflation method designed by the Inventors detected stabilization of treated ocular tissue when the other methods were not sensitive enough to register a change in modulus.

Example 4

Figure 4:
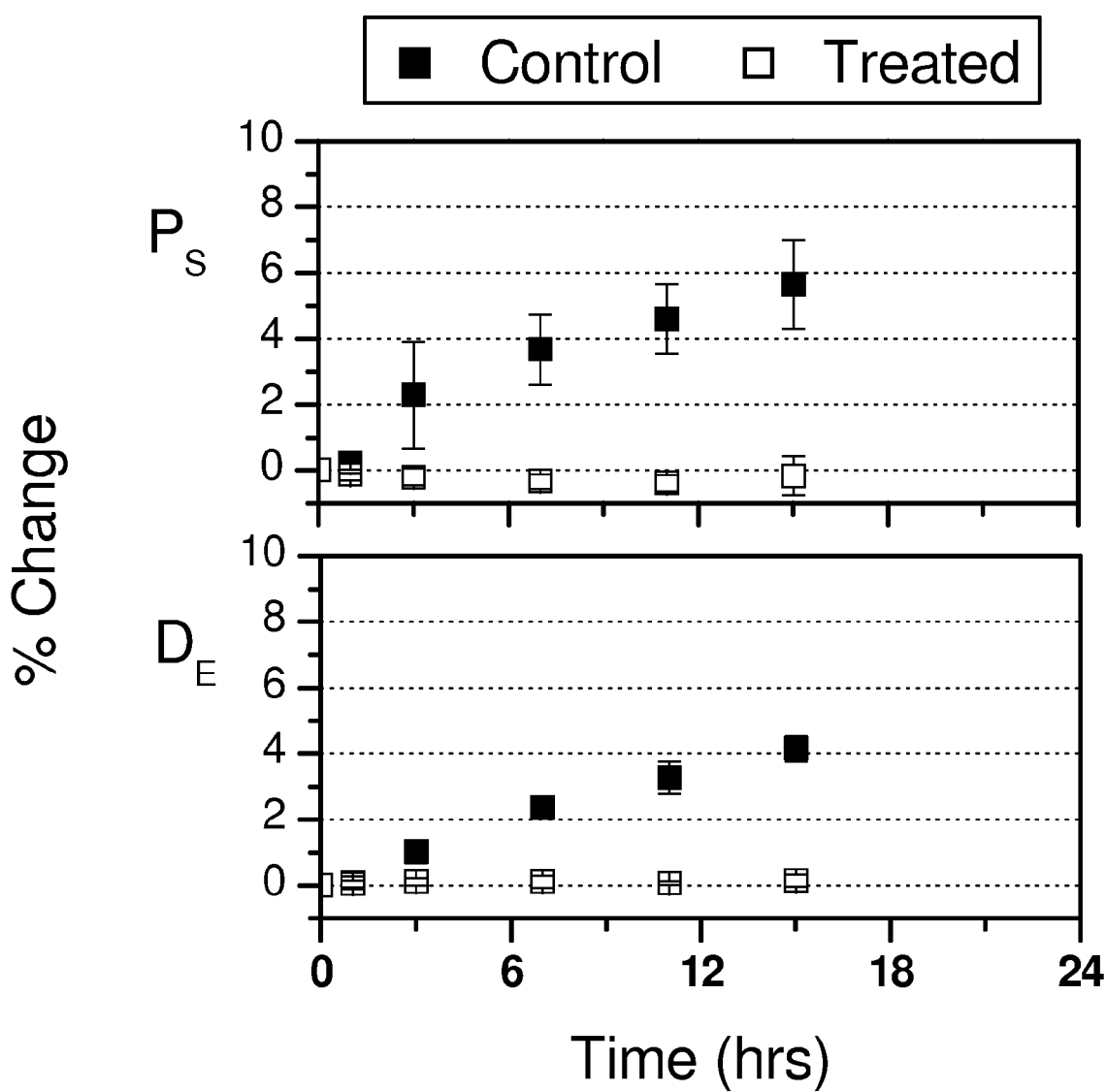
FIG. 4 shows exemplary data from ocular inflation studies where three pairs of treated and fellow control eyes (12959 and DPBS respectively) were subjected to an elevated IOP. Time t=0 corresponds to measurements after 1 hour of 85 mmHg IOP. Changes in PS and DE demonstrate the UV activated 12959's ability to stabilize the sclera.

Correlation of Mechanical Properties to Eye Elongation and In-Vitro Stabilization of Ocular Shape Inflation Model of Myopia Tests with the UV activated photoinitiator, 12959, showed the ability of this method to stabilize tissue directly Eyes were soaked in 0.3% 12959 for 5 min and exposed to light (10 mW/cm$^2$, 365 nm) for 10 min on the anterior portion of the eye and 10 min on the posterior portion. Eyes were then connected to the saline reservoir and the pressure was raised immediately to 85 mmHg Over time, the treated eyes hold a steady shape while the untreated eyes continuously expand (FIG. 4).

Figure 5:
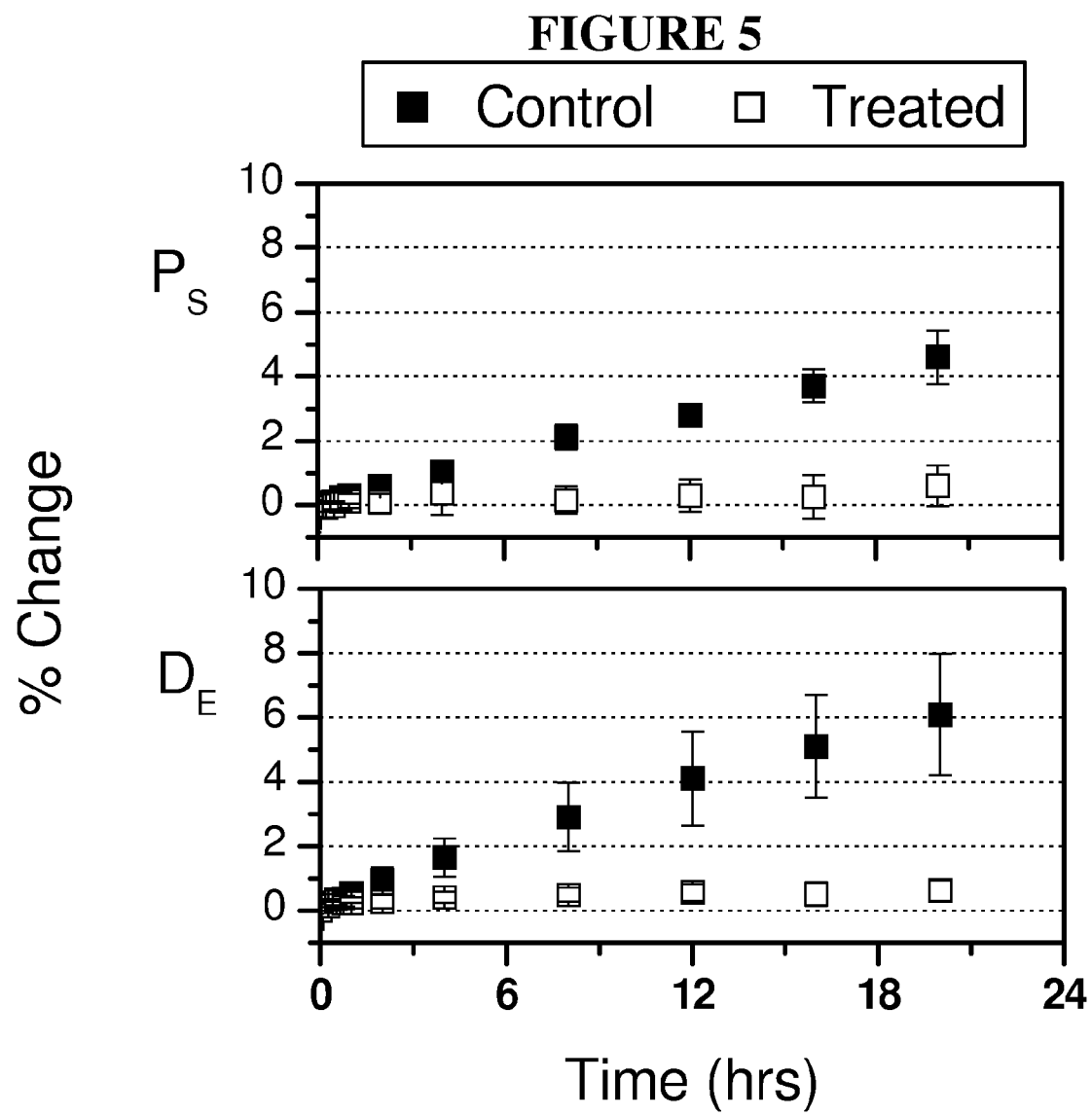
FIG. 5 shows exemplary data from ocular inflation studies where five pairs of treated and fellow control eyes (Eosin Y/TEOA and DPBS respectively) were subjected to an elevated IOP. Time t=0 corresponds to IOP being raised from normal levels to 85 mmHg Changes in PS and DE demonstrate the visible light activated Eosin Y's ability to stabilize the sclera over the 24 hour period.

Tests with 12959 proved the possibility to strengthen eye tissue and prevent expansion; however, a visible light activated formulation would generally be better suited for clinical application. Eyes were soaked in a 0.0289 mM Eosin Y/90 mM TEOA solution for 5 min, and then activated by exposure to visible light (34 mW/cm$^2$, 450-550 nm) for 5 min on the anterior and 5 min on the posterior portion of the eye. This treatment was also able to prevent eye expansion (FIG. 5).

Because of the sensitivity of the ocular shape inflation studies, we were able to proceed with low concentration formulations. The visible light activated system exemplified by Eosin Y/TEOA showed quick treatment time with low intensity, visible light exposure and low photoinitiator concentrations similar to concentrations used in FDA approved pharmaceuticals incorporating Eosin Y/TEOA.

Example 5

Toxicity Studies

Toxicity studies were performed to determine if the formulations and light exposures described above were suitable to use in an animal model for myopia and in clinical trials. Extensive literature exists that documents the biocompatibility of Eosin Y and TEOA. Because of such a promising history of low toxicity, this formulation showed great potential for biocompatibility in the eye. In order to test the in-vivo response to Eosin Y/TEOA and visible light exposure, the following experiment with various delivery techniques was used.

Six adult New Zealand White rabbits were given general anesthesia with 1-5% inhaled isofluorane administered by mask and topical 0.5% proparacaine to the right eye (OD). The right eye of each animal was sterilized with 5% betadyne. Throughout the procedure the eye was washed with sterile ocular balanced saline solution (BSS). A 15 mm incision was made in the conjunctiva and the conjunctiva was pulled away to expose the sclera. Rabbits had 200 microliters of solution applied to the sclera in the following manners.

| Photoinitiator Delivery to Rabbit Eyes | |
|---|---|
| Group 1 | Eosin Y/TEOA mixture applied to all of the exposed sclera |
| Group 2 | Eosin Y/TEOA mixture applied to a 5 mm diameter circular area of the sclera |
| Group 3 | Eosin Y/TEOA vehicle applied to all of the exposed sclera (Control) |

After 5 minutes, the treated area was photoactivated by exposure to light (~450-550 nm~34 mW/cm$^2$) for 5 minutes. The incisions in the conjunctivas were closed with suturing. All animals received subconjunctival injections of celestone (75-150 microliters) and cepahzolin (75-150 microliters). All animals were given injections of carprofen (5 mg/kg) and buprenorphine (0.05 mg/kg) and 2-3 drops of neomycin, polymixin B sulfates, gramicidin OD. Eyes were examined for any signs of pain or inflammation such as redness of the eye, discharge, ptosis of the eyelid, blepharospasm, or photophobia. Eyes were examined once a day for 1 week then once a week for 3 additional weeks. After 4 weeks all animals were euthanized and the treated eyes were removed, fixed in 10% formalin, and processed for light microscopic examination (Eosin/hematoxylin stain). The presence of any inflammatory cells was noted.

Figure 6:
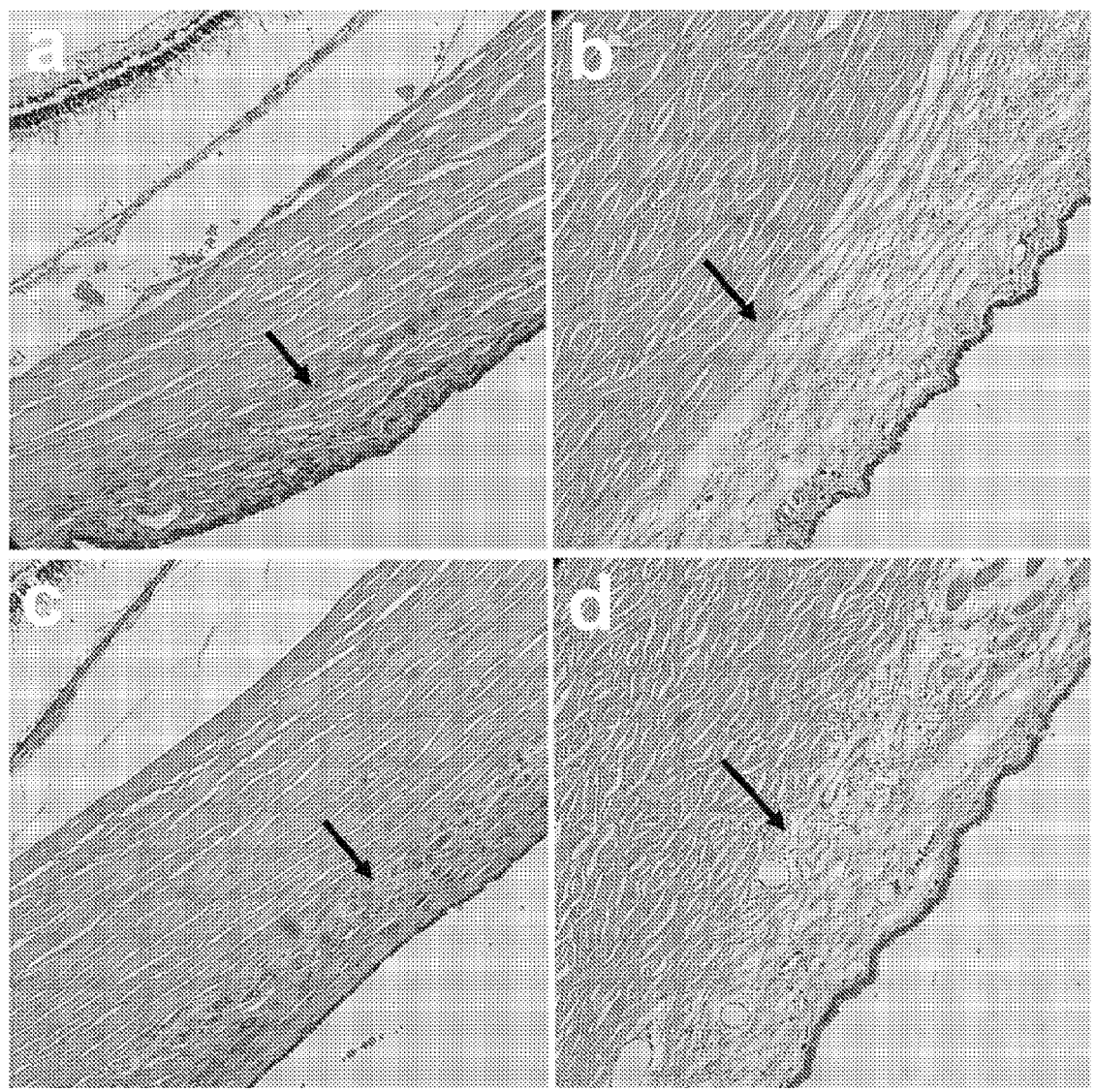
FIG. 6 shows exemplary tissue sections from histopathological examination of Eosin Y/TEOA (Group 2) and Eosin Y/TEOA vehicle (Group 3) treated rabbit eyes. a) Irradiated area of a Group 2 rabbit showing mild inflammation and moderate scarring. b) Area of a Group 2 rabbit where the conjunctiva was not retracted showing normal sclera and conjunctiva. c) Irradiated area of a Group 3 (control) rabbit showing mild inflammation and moderate scarring. d) Area of a Group 3 rabbit where the conjunctiva was not retracted showing normal sclera and conjunctiva. Arrows in all figures indicate the scleral/conjunctival border where inflammation and scarring were noted.

There was some swelling and inflammation of all operated eyes for 2 days following the procedure. This was consistent with what would be expected to result from the surgical procedure itself. Representative results are shown in FIG. 6. There were no signs of pain or inflammation in any of the eyes 3 days after the procedure and on each examination thereafter. Upon histological examination there was mild inflammation and moderate scarring along the conjunctival sclera border under the irradiated area in animals in Group 1 and 2. There was also some inflammation and scarring in the control eyes of Group 3. The irises, retinas, and ciliary bodies were all normal in appearance in all experimental groups.

There was no significant difference in the sclera of treated and control eyes, indicating that the mild inflammation and scarring which occurs is a result of the surgery and not of the treatment. Likewise, the viability of cells in the nearby tissues of the treated eyes matches that of normal eyes.

Example 6

Figure 7A:
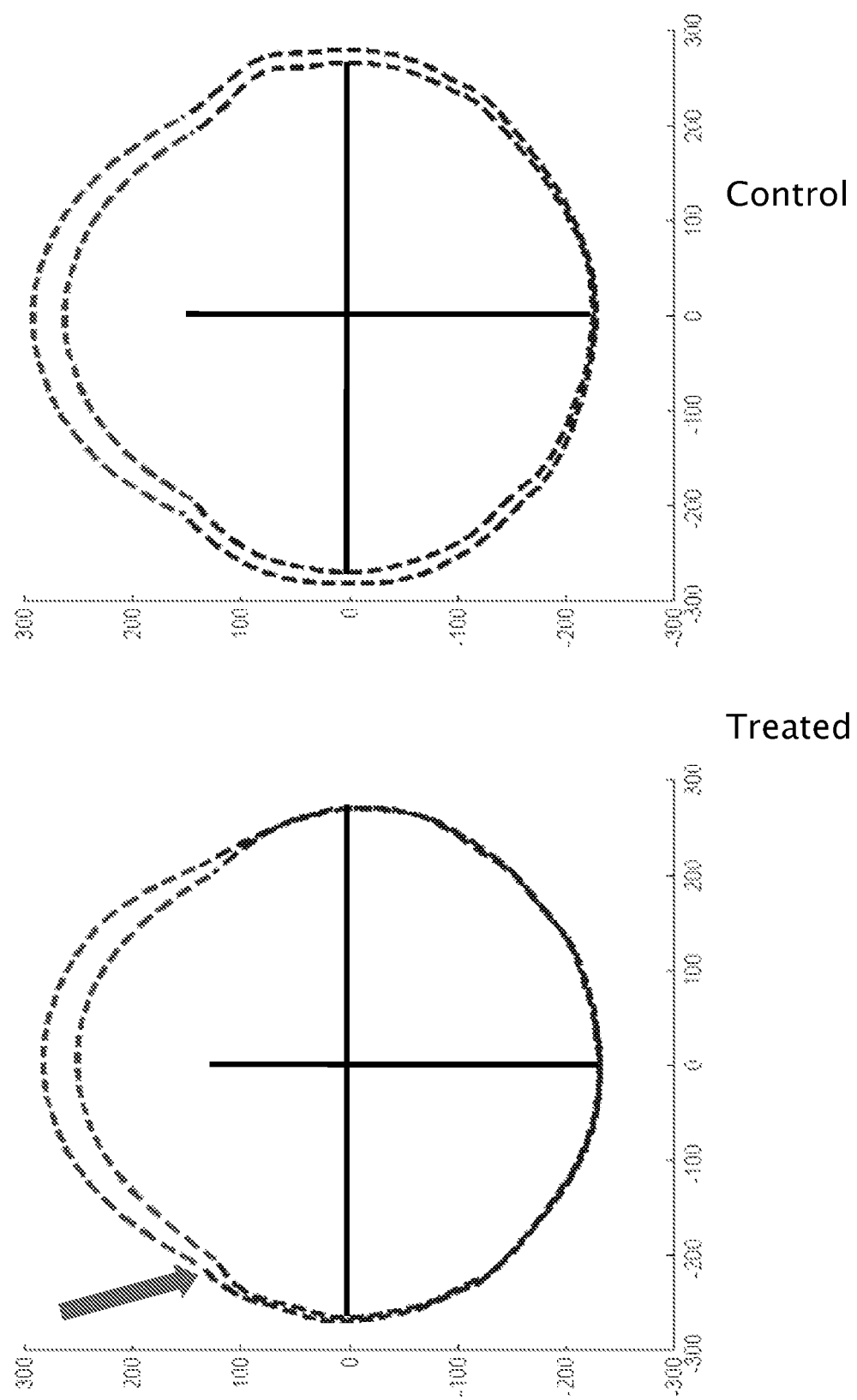
Figure 8B:
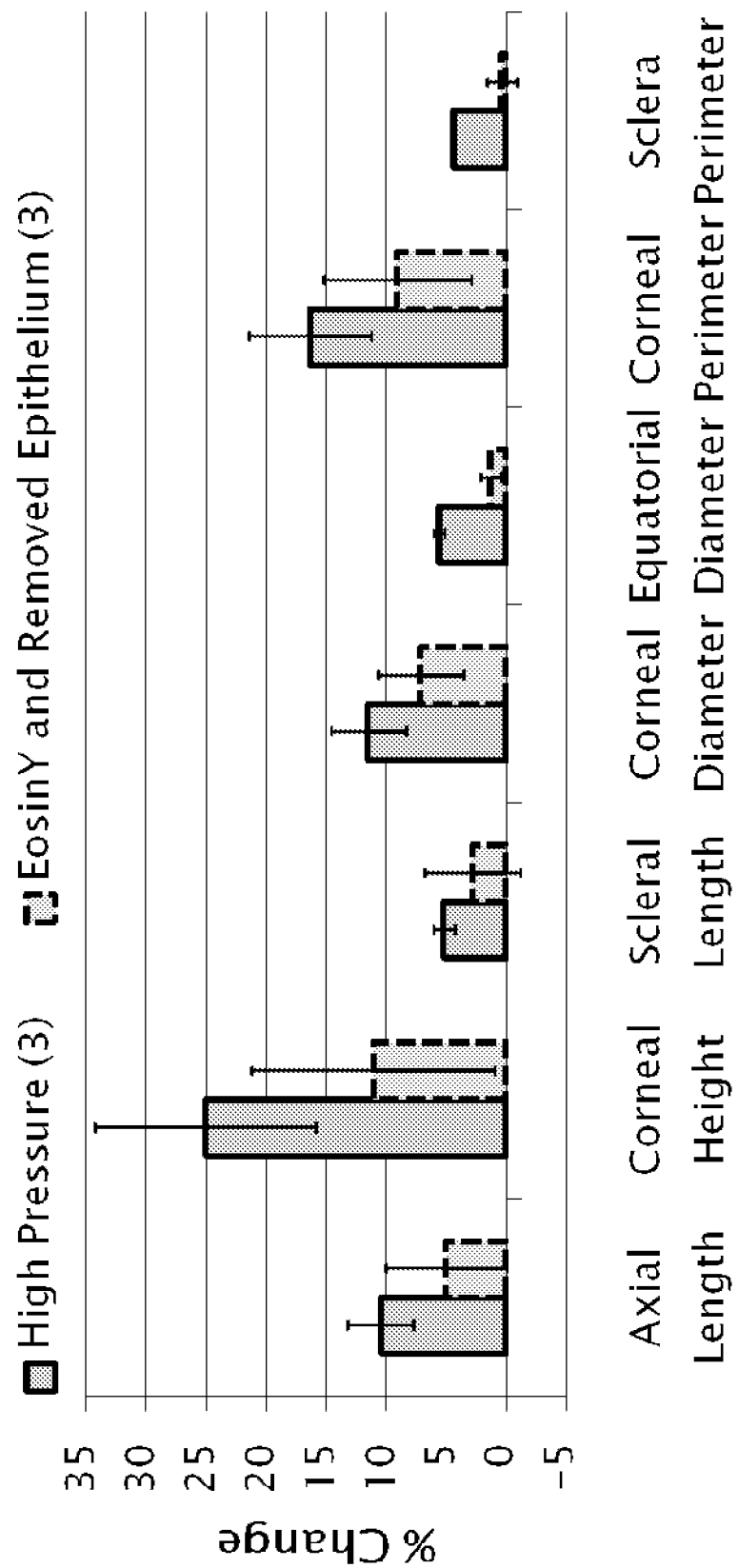

Correlation of Mechanical Properties to Eye Elongation and In-Vitro Stabilization of Ocular Shape in Inflation Model of Keratoconous The ocular shape inflation model is well suited for testing corneal strengthening as a therapy for keratoconous (FIGS. 7 & 8). As shown in FIG. 7, using the brief Eosin Y/TEOA treatment step described above did not allow sufficient photoinitiator to penetrate the cornea for subsequent corneal strengthening by direct photoinitiator crosslinking. This is in comparison with the sclera which sufficiently absorbs photoinitiator to permit adequate tissue strengthening under the parameters tested in this model system. Sufficient corneal photoinitiator absorption may be achieved by removal of the epithelium covering the cornea to allow direct application of the photoinitiator to the target tissue (FIG. 8). This resulted is complete prevention of corneal distension in the ocular inflation model system (FIG. 8). Drug ability to penetrate the epithelium can be enhanced by the co-administration of molecules designed to alter the chemical or physical nature of the epithelium (Sasaki H, Yamamura K, Mukai T, Nishida K, Nakamura J, Nakashima M, Ichikawa M. Enhancement of Ocular Drug Penetration. Critical Reviews in Therapeutic Drug Carrier Systems. 1999; 16(1):85-146). With appropriate drugs that disrupt the epithelial barrier, epithelia removal will be unnecessary. For example, there are reports of 4-fold increases in drug delivery to the aqueous after use of topically applied proparacaine (Ehlers W, Crouch E, Williams P, Riggs P. Factors Affecting Therapeutic Concentration of Topical Aminocaproic Acid in Traumatic Hyphema. IOVS. 1990; 31(11):2389-2394). In particular, topical anesthetics such as proparacaine and tetracaine alter the functioning of sodium ion channels and thereby alter the electrophysiology of the epithelium. Changes to the potential difference across the epithelium facilitate diffusion of charged molecules such as those represented by Formula I. In addition, these anesthetics alter the cell to cell binding in the epithelium, reducing its effectiveness as a barrier. In this alternative approach, drops of ophthalmic proparacaine (e.g. 0.5% drops) or drops of tetracaine (e.g. 0.5% drops) are applied to the cornea with epithelium intact. After approximately 15 min., the cornea are treated according to the methods herein.

Example 7

Modification of Eosin Y for Epithelial Penetration

While the above describe epithelial removal procedure is an acceptable medical procedure for treating the eye, the Inventors have demonstrated that Eosin Y is amenable to chemical modification which improves its penetration into the sclera and cornea with the epithelium in tact. In one example, Polyethylene glycol (PEG) is covalently bound to the carboxyl group of Eosin Y (FIG. 9), which allows PEG-Eosin Y to be dissolved in water despite reducing the charge on the molecule. This chemical modification enhances Eosin Y penetration into tissue and reduces the amount of chemical required to achieve sufficient tissue strengthening. Covalent modification with PEG also alters the photochemical activity and can influence the efficiency and time course of photoinitiator therapy. The improved penetration resultant from modifications should generally be balanced against the desired time course of irradiation to optimize treatments. For example, mixtures of Eosin Y and PEG-Eosin Y may be used to achieve both optimize photoiniator penetration and the time course of irradiation.

Figure 10:
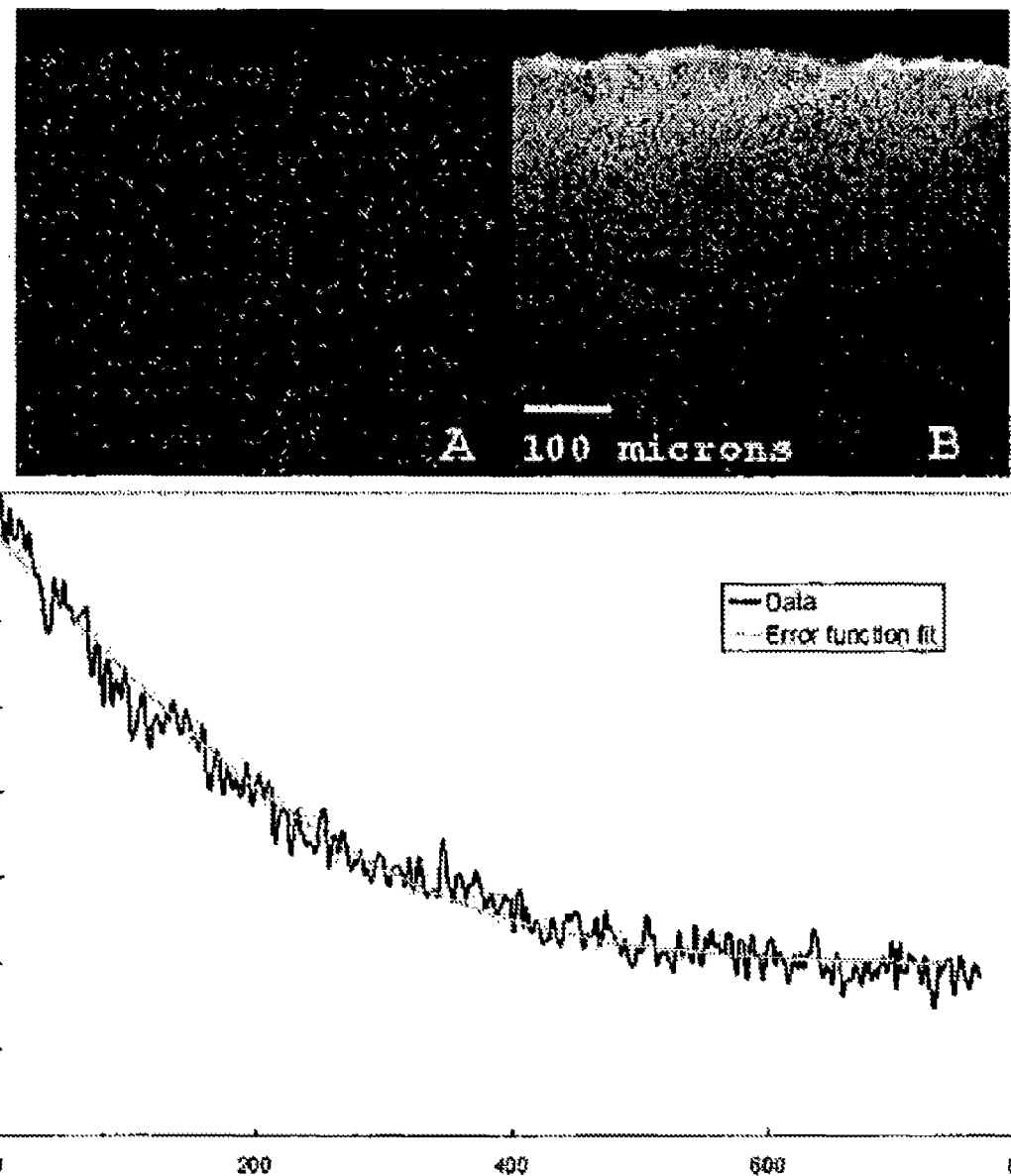
FIG. 10 reproduces confocal microscopy images showing (FIG. 10A) background fluorescence of sclera, and (FIG. 10B) penetration of fluorescein labeled PEG-acrylate after 10 minutes of incubation. The plot shows the normalized average intensity of fluorescence as a function of depth in the sclera after a 10 minute incubation and subsequent irradiation.

Exemplary studies were performed using fluorescein-grafted PEG bearing an acrylate at the opposite end of the chain (Fluorescein, another compound within the genus defined by Formula I, has similar size and hydrophobicity to Eosin Y and other candidate photoinitiators defined by Formula I). Intact porcine globes were immersed in a solution of PEG-fluorescein and 12959 in DPBS for specified times. Then, the porcine eyes were irradiated with 365 nm light to induce covalent coupling of the fluorescein to the tissue. (photocrosslinking by 12959 serves to immobilize the PEG-drug so that its distribution can be imaged.) The resulting depth profile of fluorescein in treated sclera was imaged in a tissue section cut through the thickness of the sclera. The model PEG-photoinitiator conjugate penetrated hundreds of microns into the tissue within a matter of minutes (FIG. 10). After 5 minutes of contact with a solution of PEG-drug conjugate, penetration to 100 microns or more is evident in the fluorescence micrograph of the tissue section. After 30 minutes of contact with a solution of PEG-drug conjugate, penetration to 500 microns was observed. These results indicate that topical application over a period of 5 to 30 minutes is adequate for a suitably modified drug to reach depths at which tissue reinforcement is desired.

Figure 11A:
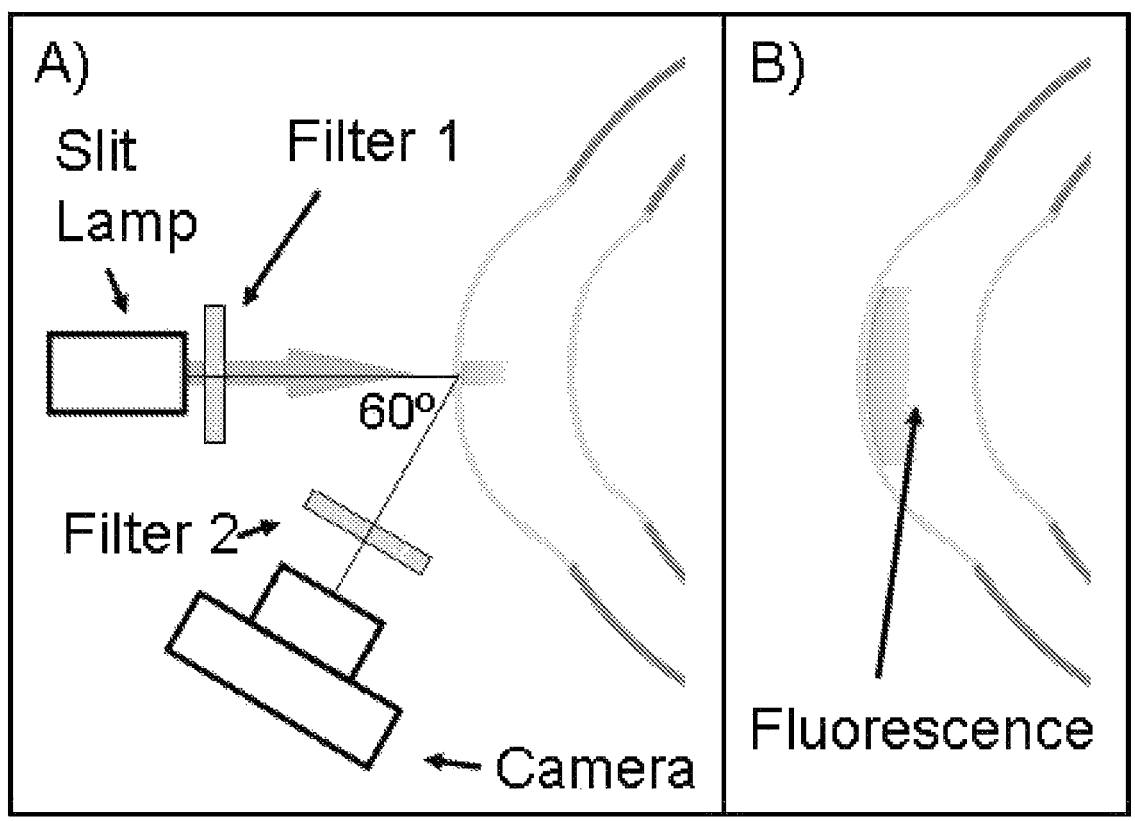
FIG. 11A shows and exemplary slit lamp apparatus used to measure drug diffusion into tissue such as the cornea. A) Top view of setup. B) Fluorescence as seen from the camera.

For Eosin Y and PEG-Eosin Y studies with porcine eyes, an assay method was utilized that relies on a modified slit lamp which can conveniently be transformed into a clinical device (FIG. 11A). Modifications have been made to allow replacement or removal of Filters 1 and 2, to place a digital camera at a consistent, fixed angle from the slit source, and to hold enucleated porcine eyes in the correct location during examination.

The fluorescence of Eosin Y enables us to view its penetration profile in the stroma with the use of proper filtering of the light source (Filter 1 passes 500±20 nm) and the light scattering from the cornea (Filter 2 passes 560±25 nm). Use of these filters allows us to distinguish scattered light from fluorescence. Untreated corneas show no fluorescence (field appears dark with both filters in place). In freshly enucleated, treated porcine eyes we are able to determine the fluorescence profile throughout the corneal thickness (FIG. 11B). Using the MATLAB® program to analyze digital images from the apparatus, the sfotware defines the corneal surface, averages the intensity of the image at different depths in the cornea, and plots the intensity versus depth. In this manner, we are able to examine the amount of drug that crosses the epithelium and its distribution in the stroma.

Enucleated eyes from 3-4 month old swine were obtained from Sierra for Medical Science. Fresh eyes were shipped in saline, on ice. On arrival, the eyes were immediately (<42 hours post-mortem) cleaned by removing the tissue still attached to the eye. Then the cornea was photographed in both scattering mode and fluorescence mode, providing baseline comparisons for background fluorescence and initial dimensions of the cornea. The epithelium was either removed with a scalpel or left intact before the eye was placed in 2 ml of treatment solution (Table 2). Eyes were left in solution for 1 hour and then removed, rinsed with approximately 4 ml of Dulbecco's PBS and photographed in both scattering and fluorescence mode. Next, the eyes with intact epithelia were debrided and photographed again. Removal of the epithelium at this step isolates fluorescence due to drug that had penetrated into the stroma.

TABLE 2

Treatment solutions mixed in Dulbecco's phosphate buffered saline.

| Treatment Solutions | EosinY (mM) | Triethanolamine (mM) |
| --- | --- | --- |
| 1 | 0.0289 | 90 |
| 2 | 1 | 90 |
| 3 | 10 | 225 |

Figure 12:
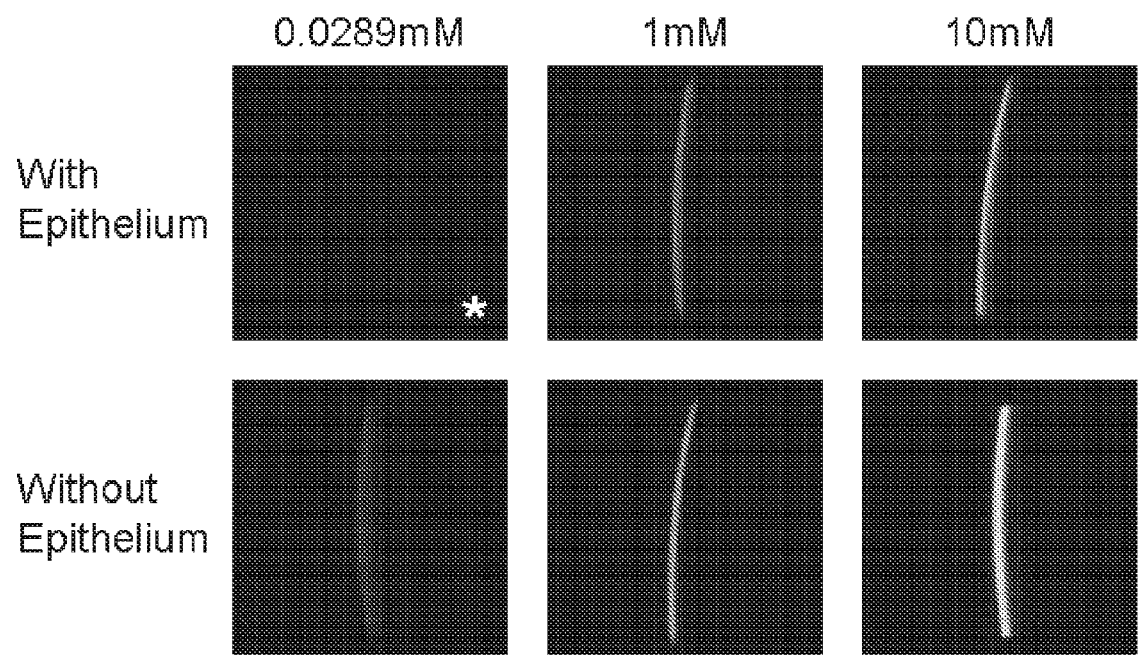
FIG. 12 shows slit lamp images of the stroma of enucleated porcine eyes that were treated either with their epithelium left intact (top row) or after de-epithelialization (bottom row) by immersion for 1 hour (or * 6 hours) in treatment solutions (Eosin Y concentration above each column corresponds to formulation in Table 2).

Penetration of Eosin Y into the stroma with and without the epithelium present (FIG. 12), demonstrates that the epithelium inhibits penetration of Eosin Y into the cornea. Significant penetration of Eosin Y across the epithelium is evident in corneas treated with high concentration solutions (2 and 3) thus demonstrating that epithelial removal may be avoided by applying a sufficient concentration of photoinitiator, in particular photoiniators represented by Formula I. In addition to images of the stroma alone (FIG. 12), images taken with the epithelium present indicate that the epithelium absorbs Eosin Y. These results show that the Eosin Y molecule may be modified to increase penetration into the stroma by increasing epithelial permeability and suggest that drug absorbed by the epithelium may possibly be released over time into the stroma, allowing for variations in the method of drug delivery and treatment time.

Example 8

Prophetic

Determine the Optimum Conditions to Stabilize the Scleral and Corneal Shape In Vitro Stabilization of eye shape—New Zealand white rabbit kit eyes will be used to study the ability of light activated compounds to strengthen the sclera. Following the procedures developed above, whole rabbit eyes are cleaned of all fat, soaked in treatment solution, irradiated with light to activate the treatment, and then mounted in a DPBS bath and connected through a hypodermic needle to a raised saline reservoir. The height of the reservoir is adjusted to give an IOP of 85 mmHg, and pictures taken over 24 hours to monitor the shape change. Procedure variables that could change the degree of stabilization will be studied with this test. Some variables to be tested include:

Photoinitiator concentration and ratio of constituent components: Minimizing the amount of photoinitiator necessary for stabilization should reduce the risk of toxicity, while increasing the amount of photoinitiator could reduce treatment time. Increasing the photoinitiator concentration would increase the number of radicals generated, but at some concentration, absorption by the dye could limit penetration of light, and only allow activation on the scleral corneal surface. In addition, the two component system of Eosin Y and TEOA may not show optimum activation at the current ratio of components. Ranges of Eosin Y concentration from 0.0289 mM to 1 mM and TEOA concentration from 3 mM to 90 mM will be tested.

Photoinitiator contact time during topical application to the sclera surface: Topical application relies on diffusion of Eosin Y and TEOA into the sclera. Increasing the contact time should increase photoinitiator concentration within the tissue and increase the penetration depth, but would also increase the patient's risk of complications. Soaking times from 1 min up to 20 min will be used to examine the effects of increased diffusion times.

Delay time between photoinitiator application and irradiation: In the time between rinsing photoinitiator off the sclera and irradiation with light, diffusion of the photoinitiator still occurs. The initial concentration gradient that results from topical application will become more uniform with time. Crosslinking within the tissue is related to the concentration of photoinitiator present. The stabilization effect of creating gradient and more uniform crosslinking will be studied by extending this delay time for as long as 20 min.

Irradiation protocol: The current procedure to achieve stabilization employs 5 min of broadband light exposure (450-550 nm @ 34 mW/cm$^2$) filtered from a Thermo Oriel 500 Watt Mercury Xenon Arc Lamp. While this dosage falls under maximum permissible exposure limits according to ANSI standards, reductions in time and intensity would further increase the safety of this procedure. Eosin Y has a peak absorption at 514 nm and matching the irradiation wavelength to this should improve efficiencies. Based on the absorption spectrum of Eosin Y and the spectral output of the Mercury Xenon lamp, calculations for a narrow bandwidth (28 nm) source centered at 514 nm predict intensities approaching half the current levels (15 mW/cm$^2$) for an equivalent irradiation protocol. Exposure times and intensity will be reduced to determine the minimum irradiation time necessary for treatments. Our preliminary results surprisingly demonstrate that an LED emitting at 525 nm and with a power of only ~7 mW/cm$^2$ over five minutes is sufficient to stabilize the shape of an eye in our ocular inflation model.

Example 9

Prophetic

Strengthening the Sclera and/or Cornea In Vivo

In-vivo treatments, in particular therapeutic treatments, will generally involve photoinitiator and light delivery to the sclera or cornea of a subject.

New Zealand White rabbits will be anesthetized with 1-5% inhaled isofluorane by administration via a mask, and topical 0.5% proparacaine. The eyes will be sterilized with 5% betadyne. Throughout the procedure the eyes will be washed in ocular balanced saline solution (BSS). An incision will be made in the conjunctiva, and retractors will be used to expose the periorbital space. Variations in the final procedural steps will be used to independently study the effects of delivery, and activation.

Photoinitiator delivery: Photoinitiator will be injected into the retrobulbar space for scleral treatment or added as drops onto the cornea (with or without de-epithelialization). In order to increase contact time, viscosity of the photoinitiator solutions will be increased using mixtures of an ophthalmic viscoelastic (e.g. Rayflo, Rayner Intraocular Lenses, Ltd.). The formulations will be left in contact for durations determined as optimal from the in vitro ocular shape inflation model. Excess photoinitiator will then be flushed out with BSS. Immediately after the rinse, animals will be euthanized. The presence of photoinitiator in the scleral and/or cornea, and surrounding tissue, of enucleated eyes will be evaluated using confocal microscopy to determine the concentration of Eosin Y as shown above for PEG-fluorescein (FIG. 10). The fluorescent signature of Eosin Y present in the micrographs will be analyzed to determine lateral spread and penetration depth.

Light delivery: Localization of the crosslinking to treat specific regions of the sclera will be attempted with a fiber optic coupled to an argon laser (514 nm) or an LED (525 nm). According to photoinitiator delivery methods determined in the in vitro work described above, a fluorescently labeled tracer molecule that binds to tissue upon light activation will be given in conjunction with the photoactivator formulation. Excess formulation will be flushed from the periorbital space and/or from the corneal surface. Sufficient light will be delivered to the sclera and/or cornea through the fiber source to initiate crosslinking (intensity and duration as determined above). The eye will be washed with BSS, the rabbits euthanized and the eyes enucleated. Crosslinking will be evaluated for depth and precision of activation using fluorescence microscopy.

Toxicity: Groups of 6 rabbits will receive complete treatments using optimized conditions determined according to the examples above. Control groups will receive the tested photoinitiator formulations without light activation or light therapy with a vehicle formulation. After photoinitiator and light delivery, the eye will be flushed with BSS to remove excess formulation. The surgical incision will be closed with sutures. The animals will be given subconjunctival injections of cefazolin (antibiotic) and celestone (steroid). The eyes will be examined clinically for any signs of pain or inflammation, such as redness of the eye, pus in the eye, and ptosis of the eyelid once a day for 1 week, then once a week for 1 month. After 1 month the animals will be euthanized. The treated eyes will be removed, fixed in 10% formalin and processed for light microscopic examination. The presence of any inflammatory cells will be noted. The clinical and histopathological inflammatory response will be graded on a 1 to 4 scale with 1 equal to no inflammation, 2 equal to mild inflammation and 3 equal to moderate inflammation and 4 equal to severe inflammation.

Example 10

Prophetic

Strengthening the Sclera and/or Corneal In Vivo

In-vivo Treatment, Ex-vivo stabilization: Following in vivo application as described above, eyes will be tested ex vivo for stabilization. One eye will be treated and the second eye will serve as a control. The rabbits will be euthanized at various times post-treatment (Table 3). Enucleated eyes will be tested for stabilization using the pressure induced, ocular inflation assay described above.

TABLE 3

Ex-vivo Treatment Efficacy Test in Rabbits

| Group | Post-Treatment Time |
|---|---|
| E | 1 week |
| F | 1 month |
| G | 3 months |
| H | 6 months |

The eyes from one or more groups will maintain their shape when subjected to 85 mmHg IOP in an ocular inflation assay performed as described above.

Example 11

Prophetic

Strengthening the Sclera and/or Corneal In Vivo in a Myopia Model System

A model of form deprivation myopia in guinea pigs has been established (Howlett M H, McFadden S A., Form-deprivation myopia in the guinea pig (Cavia porcellus), Vision Res. 2006 January; 46(1-2):267-83, Epub 2005 Aug. 31). A white plastic hemisphere is placed over one eye of the guinea pig at 5 days of age. After only 11 days of form deprivation, there is an average of −6.6 D more myopia and 146 nm axial elongation compared to the unoccluded fellow eye. This model will be used to further validate the photoinitiator formulations and use parameters from the foregoing experiments.

The experiment will test normal vs. myopic eyes (Group A), normal vs. treated myopic (Group B), treated normal vs. treated myopic (Group C), and myopic vs. treated myopic (Group D).

TABLE 4

In-vivo efficacy in Guinea Pigs Form Deprivation

| Group | Occluder | | Treatment | |
|---|---|---|---|---|
| | Eye 1 | Eye 2 | Eye 1 | Eye 2 |
| A | Yes | No | No | No |
| B | Yes | No | Yes | No |
| C | Yes | No | Yes | Yes |
| D | Yes | Yes | Yes | No |

At 4 days of age, the right eye will be prolapsed out of the eye socket and the posterior sclera exposed. This region will be treated with the photoinitiator (e.g. Eosin Y) formulations from above using a Weck Cell applicator soaked in photoinitiator solution. After waiting an appropriate time (several minutes) as determined above, the treated region will be irradiated to induce radical formation by the photoinitiator. The eye will then be replaced in the socket and the conjunctiva closed with resorbable sutures. A series of control animals will undergo an identical procedure, but without application of either photoinitiator or irradiation. At 5 days of age, Velcro arcs are glued above and below the right eye of guinea pigs in both the treated and control groups and a white plastic diffuser will be fastened to the Velcro arcs.

At 16 days of life, the diffusers will be removed and the following measurements will be performed: Infrared keratometry to determine corneal curvature; Axial length using high frequency ultrasound (20 MHz); and Refractive error using streak retinoscopy after cycloplegia. Following these measurements the animals will be sacrificed for histologic studies of the whole globes.

The eyes from treated myopic groups will maintain their shape when subjected to 85 mmHg IOP in an ocular inflation assay performed as described above or will maintain their shape in vivo as compared to control eyes.

Example 12

Prophetic

A patient with open angle glaucoma presents with elevated intraocular pressure and increased cupping of the optic nerves in both eyes. To provide mechanical stabilization of the lamina cribrosa and reduce progression of the optic atrophy, eosin Y/TEOA are injected intravitreally using a pars plana approach. Five to 60 minutes later the lamina cribrosa is irradiated using a two photon light source directed at the lamina. Resultant cross linking the connective tissue within the lamina increases its modulus and resists subsequent deformation. Targeting of the lamina with the 2 photon irradiation source can be aided with the motion sensitive optical coherence tomography device well known in the art and described for instance in U.S. Patent Application No. 2005/0048044.

Example 13

Prophetic

A patient with myopia elects to undergo LASIK. To prevent post-LASIK ectasia, eosin Y/TEOA is applied to the stromal bed following excimer ablation. The flap is then repositioned. Increased corneal stiffening from the photoitiator based treatment reduces the risk of post-LASIK ectasia.

REFERENCES

All patents and publications mentioned in the specification are indicative of the level of those skilled in the art to which the invention pertains.

Andreassen T T, Simonsen A H, Oxlund H. Biomechanical properties of keratoconus and normal corneas. Exp Eye Res. 1980; 31(4):435-41.

Avetisov, E. S., Tarutta, E. P., Iomdina, E. N., Vinetskaya, M. I. & Andreyeva, L. D. Nonsurgical and surgical methods of sclera reinforcement in progressive myopia. Acta Ophthalmologica Scandinavica 75, 618-623 (1997).

Belyaev, V. S. & Ilyina, T. S. Late Results Of Scleroplasty In Surgical Treatment Of Progressive Myopia. Eye Ear Nose And Throat Monthly 54, 109-113 (1975).

Blinder, K. J., Blumenkranz, M. S., Bressler, N. M., Bressler, S. B., Donati, G., Lewis, H., Lim, J. I., Menchini, U., Miller, J. W., Mones, J. M., Potter, M. J., Pournaras, C., Reaves, A., Rosenfeld, P., Schachat, A. P., Schmidt-Erfurth, U., Sickenberg, M., Singerman, L. J., Slakter, J., Strong, H. A., Virgili, G. & Williams, G. A. Verteporfin therapy of subfoveal choroidal neovascularization in pathologic myopia-2-year results of a randomized clinical Trial—VIP report no. 3. Ophthalmology 110, 667-673 (2003).

Binder P S, Lindstrom R L, Stulting R D, Donnenfeld E, Wu H, McDonnell P, Rabinowitz Y. Keratoconus and corneal ectasia after LASIK. J Cataract Refract Surg. 2005; 31(11): 2035-8.

Bron, A. J. Keratoconus. Cornea 7, 163-169 (1988).

Bühren J, Kühne C, and Kohnen T. Defining Subclinical Keratoconus Using Corneal First-Surface Higher-Order Aberrations. *American Journal of Ophthalmology.* 2007 143: 381-389

Chauvaud, D., Assouline, M. & Perrenoud, F. Scleral reinforcement. Journal Francais D Ophtalmologie 20, 374-382 (1997).

Chow, Y. C., Dhillon, B. B., Chew, P. T. & Chew, S. J. Refractive errors in Singapore medical students. Singapore Medical Journal 45, 470-474 (1990).

Chua W H, Balakrishnan V, Chan Y H, Tong L, Ling Y, Quah B L, Tan D. Atropine for the treatment of childhood myopia. Ophthalmology. 2006 December; 113(12):2285-91.

Chua, W. H., Tan, D., Balakrishnan, V. & Chan, Y. H. Progression of childhood myopia following cessation of atropine treatment. Investigative Ophthalmology & Visual Science 46 (2005).

Colin J, Cochener B, Savary G, and Malet G. Correcting keratoconus with intrastromal rings. *J Cataract Refract Surg* 26 (2000), pp. 1117-1122.

Curtin, B. J. The myopias: basic science and clinical management (Lippincott Williams & Wilkins, 1985).

Ehlers W, Crouch E, Williams P, Riggs P. Factors Affecting Therapeutic Concentration of Topical Aminocaproic Acid in Traumatic Hyphema. IOVS. 1990; 31(11):2389-2394.

Edwards, A. & Prausnitz, M. R. Predicted permeability of the cornea to topical drugs. Pharmaceutical Research 18, 1497-1508 (2001).

Faraj H G, Gatinel D, Chastang P J and Hoang-Xuan T. Corneal ectasia after LASIK. *J Cataract Refract Surg* 29 (2003), p. 220

Howlett M H, McFadden S A., Form-deprivation myopia in the guinea pig (Cavia porcellus), Vision Res. 2006 January; 46(1-2):267-83, Epub 2005 Aug. 31.

Hsu W M, Cheng C Y, Liu J H, Tsai S Y, Chou P. Prevalence and causes of visual impairment in an elderly Chinese population in Taiwan: the Shihpai Eye Study. Ophthalmology. 2004; 111(1):62-9.

Iwase A, Araie M, Tomidokoro A, Yamamoto T, Shimizu H, Kitazawa Y; Tajimi Study Group.Prevalence and causes of low vision and blindness in a Japanese adult population: the Tajimi Study. Ophthalmology. 2006; 113(8):1354-62.

Jacob, J. T., Lin, J. J. & Mikal, S. P. Synthetic scleral reinforcement materials.3. Changes in surface and bulk physical properties. Journal Of Biomedical Materials Research 37, 525-533 (1997).

Jacoblabarre, J. T., Assouline, M., Conway, M. D., Thompson, H. W. & McDonald, M. B. Effects Of Scleral Reinforcement On The Elongation Of Growing Cat Eyes. Archives Of Ophthalmology 111, 979-986 (1993).

Khoo C Y, Chong J, Rajan U. A 3-year study on the effect of RGP contact lenses on myopic children. Singapore Med J 1999; 40:230-7.

Korobelnik, J. F., D'Hermies, F., Chauvaud, D., Legeais, J. M., Hoang-Xuan, T. & Renard, G. Expanded polytetrafluoroethylene episcleral implants used as encircling scleral buckling—An experimental and histopathological study. Ophthalmic Research 32, 110-117 (2000).

Krachmer, J. H., Feder, R. S. & Belin, M. W. Keratoconus And Related Noninflammatory Corneal Thinning Disorders. Survey Of Ophthalmology 28, 293-322 (1984).

Kymionis G D, Siganos C S, Tsiklis N S, Anastasakis A, Yoo S H, Pallikaris A I, Astyrakakis N, Pallikaris I G. Long-term follow-up of Intacs in keratoconus. Am J Ophthalmol. 2007; 143(2):236-244.

Lin L L, Shih Y F, Hsiao C K, Chen C J, Lee L A, Hung P T. Epidemiologic study of the prevalence and severity of myopia among schoolchildren in Taiwan in 2000. J Formos Med. Assoc. 2001; 100(10):684-91.

Lodge A., Peto T. and McFadden S., Form deprivation myopia and emmetropization in the guinea pig, Proceedings of the Australian Neuroscience Society 5 (1994), p. 123.

McBrien, N. A. & Gentle, A. Role of the sclera in the development and pathological complications of myopia. Progress In Retinal And Eye Research 22, 307-338 (2003).

McDonald M B, Kaufman H E, Durrie D S et al., Epikeratophakia for the treatment of keratoconus. The nationwide study. *Arch Ophthalmol* 93 (1982), pp. 342-347.

Mortemousque, B., Leger, F., Velou, S., Graffan, R., Colin, J. & Korobelnik, J. F. S/e-PTFE episcleral buckling implants: An experimental and histopathologic study. Journal Of Biomedical Materials Research 63, 686-691 (2002).

Politzer, M. Experiences In Medical-Treatment Of Progressive Myopia. Klinische Monatsblatter Fur Augenheilkunde 171, 616-619 (1977).

Prausnitz, M. R. & Noonan, J. S. Permeability of cornea, sclera, and conjunctiva: A literature analysis for drug delivery to the eye. Journal Of Pharmaceutical Sciences 87, 1479-1488 (1998).

Rabinowitz Y S, Garbus J and McDonnell P J. Computer-assisted corneal topography in family members of patients with keratoconus. *Arch Ophthalmol* 108 (1990), pp. 365-371.

Rabinowitz, Y. S. Keratoconus. Survey Of Ophthalmology 42, 297-319 (1998).

Randleman J B. Post-laser in-situ keratomileusis ectasia: current understanding and future directions. Curr Opin Ophthalmol. 2006; 17(4):406-12.

Randleman J B, Russell B, Ward M A, et al., Risk factors and prognosis for corneal ectasia after LASIK, *Ophthalmology* 110 (2003), pp. 267-275.

Salabert D, Cochener B, Mage F and Colin J. Keratoconus and familial topographic corneal anomalies [in French]. *J Fr Ophtalmol* 17 (1994), pp. 646-656.

Sasaki H, Yamamura K, Mukai T, Nishida K, Nakamura J, Nakashima M, Ichikawa M. Enhancement of Ocular Drug Penetration. Critical Reviews in Therapeutic Drug Carrier Systems. 1999; 16(1):85-146.

Seiler, T., Huhle, S., Spoerl, E. & Kunath, H. Manifest diabetes and keratoconus: A retrospective case-control study. Graefes Archive For Clinical And Experimental Ophthalmology 238, Siatkowski R M, Cotter S, Miller J M, Scher C A, Crockett R S, Novack G D; US Pirenzepine Study Group. Safety and efficacy of 2% pirenzepine ophthalmic gel in children with myopia: a 1-year, multicenter, double-masked, placebo-controlled parallel study. Arch Ophthalmol. 2004; 122(11): 1667-74.

Shih Y F, Lin L L, Hwang C Y, et al. The effects of qi-qong ocular exercise on accommodation. Clin J Physiol 1995; 38:35-42.822-825 (2000).

Smith V A, Easty D L. Matrix metalloproteinase 2: involvement in keratoconus. *Eur J Ophthalmol.* 2000; 10:215-226.

Smith V A, Hoh H B, Littleton M, Easty D L. Over-expression of a gelatinase A activity in keratoconus. Eye. 1995; 9:429-433

Spitznas M, Eckert J, Frising M, Eter N. Long-term functional and topographic results seven years after epikeratophakia for keratoconus. Graefes Arch Clin Exp Ophthalmol. 2002; 240(8):639-43.

Sperduto, R. D., Seigel, D. D., Roberts, J. J. & Rowland, M. M. Prevalence of myopia in the United States. 405-407 (1983).

Spoerl E, Wollensak G, Seiler T. Increased resistance of crosslinked cornea against enzymatic digestion. Curr Eye Res. 2004; 29(1):35-40.

Spoerl E, Wollensak G, Dittert D D, Seiler T. Thermomechanical behavior of collagen-cross-linked porcine cornea. Ophthalmologica. 2004; 218(2):136-40.

Spoerl, E. & Seiler, T. Techniques for stiffening the cornea. Journal Of Refractive Surgery 15, 711-713 (1999).

Sporl, E., Huhle, M., Kasper, M. & Seiler, T. Artificial stiffening of the cornea by induction of intrastromal crosslinks. Ophthalmologe 94, 902-906 (1997).

Tae, G. et al. Crosslinking effects of glycerose on rabbit and human corneas: Rheological and microscopical studies. Investigative Ophthalmology & Visual Science 41, S693-S693 (2000).

Tangliu, D. D. S., Richman, J. B., Weinkam, R. J. & Takruri, H. Effects of 4 Penetration Enhancers on Corneal Permeability of Drugs in-Vitro. Journal of Pharmaceutical Sciences 83, 85-90 (1994).

Tano, Y. Lix Edward Jackson memorial lecture—Pathologic myopia: Where are we now? American Journal Of Ophthalmology 134, 645-660 (2002).

Tarutta, Y. P., Iomdina, Y. N., Shamkhalova, E. S., Andreyeva, L. D. & Maximova, M. V. Sclera Fortification In Children At A High-Risk Of Progressive Myopia. Vestnik Oftalmologii 108, 14-17 (1992).

Tessier, F. J., Tae, G., Monnier, V. M. & Kornfield, J. A. Rigidification of corneas treated in vitro with glyceraldehyde characterization of two novel crosslinks and two chromophores. Investigative Ophthalmology & Visual Science 43, U892-U892 (2002).

Tokoro, T. On the definition of pathologic myopia in group studies. Acta Opthalmol Suppl 185, 107-108 (1998).

Udar N, Atilano S R, Brown D J, Holguin B, Small K, Nesburn A B,

Kenney M C. SOD1: a candidate gene for keratoconus. Invest Ophthalmol V is Sci. 2006; 47(8):3345-51.

Wollensak, G. & Spoerl, E. Collagen crosslinking of human and porcine sclera. Journal Of Cataract And Refractive Surgery 30, 689-695 (2004).

Wollensak, G. Crosslinking treatment of progressive keratoconus: new hope. Current Opinion In Ophthalmology 17, 356-360 (2006).

Wollensak, G., Sporl, E. & Seiler, T. Treatment of keratoconus by collagen cross linking. Ophthalmologe 100, 44-49 (2003).

Wollensak G, Aurich H, Pham D T, Wirbelauer C. Hydration behavior of porcine cornea crosslinked with riboflavin and ultraviolet A. J Cataract Refract Surg. 2007; 33(3):516-21.

Wollensak G, Iomdina E, Dittert D D, Salamatina O, Stoltenburg G. Cross-linking of scleral collagen in the rabbit using riboflavin and UVA. Acta Ophthalmol Scand. 2005; 83(4):477-82.

Wollensak G, Wilsch M, Spoerl E, Seiler T. Collagen fiber diameter in the rabbit cornea after collagen crosslinking by riboflavin/UVA. Cornea. 2004; 23(5):503-7.

Wollensak G, Spoerl E. Collagen crosslinking of human and porcine sclera. J Cataract Refract Surg. 2004; 30(3):689-95.

Wollensak G, Spoerl E, Reber F, Seiler T. Keratocyte cytotoxicity of riboflavin/UVA-treatment in vitro. Eye. 2004; 18(7):718-22.

Wollensak G, Spoerl E, Wilsch M, Seiler T. Keratocyte apoptosis after corneal collagen cross-linking using riboflavin/UVA treatment. Cornea. 2004; 23(1):43-9.

Wollensak G, Sporl E, Reber F, Pillunat L, Funk R. Corneal endothelial cytotoxicity of riboflavin/UVA treatment in vitro. Ophthalmic Res. 2003; 35(6):324-8.

Wollensak G, Spoerl E, Wilsch M, Seiler T. Endothelial cell damage after riboflavin-ultraviolet-A treatment in the rabbit. J Cataract Refract Surg. 2003; 29(9):1786-90.

Wollensak G, Spoerl E, Seiler T. Riboflavin/ultraviolet-a-induced collagen crosslinking for the treatment of keratoconus. Am J Ophthalmol. 2003; 135(5):620-7.

Wong, T. Y., Foster, P. J., Hee, J. J., Ng, T. P., Tielsch, J. M., Chew, S. J., Johnson, G. J. & Seah, S. K. Prevalence and risk factors for refractive errors in adult Chinese in Singapore. Investigative Ophthalmology & Visual Science 41, 2486-2494 (2000).

Xu L, Wang Y, Li Y, Wang Y, Cui T, Li J, Jonas J B. Causes of blindness and visual impairment in urban and rural areas in Beijing: the Beijing Eye Study. Ophthalmology. 2006 113: 1134.e1-11.

U.S. PATENT APPLICATION NO. 2005/0271590

U.S. Pat. No. 6,161,544

U.S. Pat. No. 6,478,792

U.S. PATENT APPLICATION NO. 2005/0048044

All references cited or otherwise identified herein are hereby incorporated by reference in their entireties as if each had been specifically incorporated by reference above. In particular, all references are hereby incorporated by reference for the specific materials therein for which a reference has been cited or relied upon.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of altering a mechanical and/or chemical property of a tissue in a subject, the method comprising the steps of:
   (a) administering a composition comprising a photoinitiator compound to a tissue of the subject, wherein the composition does not include a photopolymerizable compound, and
   (b) activating the photoinitiator compound by a visible light irradiation of the tissue, whereby the photoinitiator compound directly alters a mechanical and/or chemical property of the tissue.

2. The method of claim 1 wherein the method is further defined as strengthening the tissue, stabilizing the tissue shape, changing the shape of the tissue, or a combination thereof.

3. The method of claim 1 wherein the tissue is an ocular tissue.

4. The method of claim 3, wherein the ocular tissue includes at least a portion of a cornea and/or a sclera.

5. The method of claim 3, wherein the ocular tissue includes at least a portion of a lamina cribrosa.

6. The method of claim 4, wherein the tissue includes at least a portion of the cornea, the method is performed substantially concurrently with a corneal operation and the photoinitiator compound is provided in a therapeutically effective amount which directly reduces the risk of a post operative corneal deformation condition.

7. The method of claim 1, wherein
a) the subject has or is at risk of developing an ocular deformation condition comprising one or more of keratoconus, post-laser-assisted in situ keratomileusis (LASIK) ectasia, post-photorefractive keratectomy (PRK) ectasia, post-infection ectasia, peripheral ectasia, rheumatoid condition of the cornea, degenerative myopia, regular myopia, scleral staphyloma, ocular hypertension glaucoma, or low tension glaucoma,
b) the photoinitiator compound is provided in a therapeutically effective amount which directly treats or directly reduces the risk of the ocular deformation condition, and
c) the visible light irradiation occurs over a period of 30 minutes or less.

8. The method of claim 7, wherein the subject has corneal ectasia.

9. The method of claim 7, wherein the subject has keratoconus.

10. The method of claim 7, wherein the subject has degenerative myopia.

11. The method of claim 1, wherein the photoinitiator compound comprises a photoinitiator, a PEG-photoinitiator, or a combination thereof, the photoinitiator having the structure of Formula I:

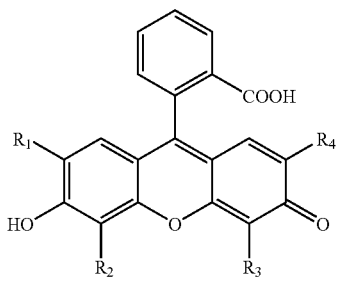

wherein $R_1$, $R_2$, $R_3$, and $R_4$ are each independently H, halogen, or $NO_2$ or pharmaceutical salts thereof.

12. The method of claim 11, wherein $R_1$, $R_2$, $R_3$, and $R_4$ are each independently H, Br, or $NO_2$.

13. The method of claim 11, wherein the photoinitiator compound comprises Eosin Y, Eosin B or fluorescein.

14. The method of claim 11, wherein the visible light irradiation occurs over a period of 30 minutes or less.

15. The method of claim 11, wherein the visible light irradiation occurs over a period of 20 minutes or less.

16. The method of claim 11, wherein the visible light irradiation occurs over a period of 10 minutes or less.

17. The method of claim 11, wherein the visible light irradiation occurs over a period of 5 minutes or less.

18. The method of claim 1, wherein the administering step is further defined as administering the photoinitiator compound topically or by injection.

19. The method of claim 1, wherein the photoinitiator compound is a Type II photoinitiator, and wherein the composition further comprises a co-initiator.

20. The method of claim 19, wherein the photoinitiator compound is Eosin Y and the co-initiator is triethanolamine.

21. The method of claim 1, wherein the visible light irradiation occurs over a period of 30 minutes or less.

22. The method of claim 1, wherein the visible light irradiation occurs over a period of 20 minutes or less.

23. The method of claim 1, wherein the visible light irradiation occurs over a period of 10 minutes or less.

24. The method of claim 1, wherein the visible light irradiation occurs over a period of 5 minutes or less.

25. A method of treating or reducing the risk of an ocular deformation condition in a subject, the method comprising the steps of:
a) administering a composition comprising a photoinitiator compound in a therapeutically effective amount, wherein the composition does not include a photopolymerizable compound, to directly treat, or directly reduce the risk of an ocular deformation condition in, an ocular tissue of the subject; and
b) activating the photoinitiator compound by a light irradiation of the tissue,
whereby the photoinitiator compound directly treats or directly reduces the risk of the ocular deformation condition.

26. The method of claim 25 wherein the photoinitiator compound is provided to treat an ocular deformation condition and the therapeutically effective amount of the photoinitiator compound treats a symptom of the ocular deformation condition by strengthening the ocular tissue, stabilizing the ocular tissue shape, changing the shape of the ocular tissue, or a combination thereof.

27. The method of claim 25, wherein the ocular tissue includes at least a portion of a lamina cribrosa, a cornea and/or a sclera.

28. The method of claim 25, wherein the subject has an ocular deformation condition comprising one or more of keratoconus, post-laser-assisted in situ keratomileusis (LASIK) ectasia, post-photorefractive keratectomy (PRK) ectasia, post-infection ectasia, peripheral ectasia, rheumatoid condition of the cornea, degenerative myopia, regular myopia or scleral staphyloma, ocular hypertension glaucoma, or low tension glaucoma.

29. The method of claim 25, wherein the ocular deformation condition is degenerative myopia.

30. The method of claim 25, wherein the ocular deformation condition is keratoconus.

31. The method of claim 25, wherein the photoinitiator compound comprises a compound defined by Formula I:

a.

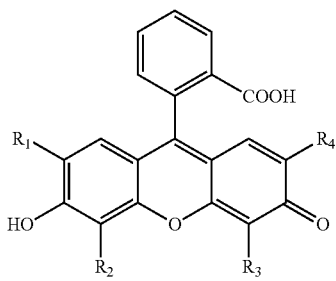

wherein $R_1$, $R_2$, $R_3$, and $R_4$ are each independently H, halogen, or $NO_2$ or pharmaceutical salts thereof.

32. The method of claim 31, wherein the photoinitiator compound comprises a polyethylene glycol derivative of the compound represented by Formula I.

33. The method of claim 31, wherein the light irradiation occurs over a period of 30 minutes or less.

34. The method of claim 31, wherein the light irradiation occurs over a period of 20 minutes or less.

35. The method of claim 31, wherein the light irradiation occurs over a period of 10 minutes or less.

36. The method of claim 31, wherein the light irradiation occurs over a period of 5 minutes or less.

37. The method of claim 25, wherein the photoinitiator compound is capable of directly treating or reducing the risk of the ocular deformation condition upon illumination of the photoinitiator compound for 30 minutes or less using light comprising a wavelength of 500±50 nm at an illumination intensity of from 1-100 mW/cm².

38. The method of claim 25, wherein the photoinitiator compound is provided by topical administration.

39. The method of claim 25, wherein the photoinitiator compound is provided by injection.

40. The method of claim 25, wherein the ocular tissue includes at least a portion of the cornea, the method is performed substantially concurrently with a corneal operation and the photoinitiator compound is provided in a therapeutically effective amount which directly reduces the risk of a post operative corneal deformation condition.

41. The method of claim 25, wherein the light irradiation occurs over a period of 30 minutes or less.

42. The method of claim 25, wherein the light irradiation occurs over a period of 20 minutes or less.

43. The method of claim 25, wherein the light irradiation occurs over a period of 10 minutes or less.

44. The method of claim 25, wherein the light irradiation occurs over a period of 5 minutes or less.

45. The method of claim 25, wherein the photoinitiator compound is a Type II photoinitiator, and wherein the composition further comprises a co-initiator.

46. The method of claim 45, wherein the photoinitiator compound is Eosin Y and the co-initiator is triethanolamine.

47. The method of claim 46, wherein the light irradiation occurs over a period of 30 minutes or less.

48. The method of claim 46, wherein the light irradiation occurs over a period of 20 minutes or less.

49. The method of claim 46, wherein the light irradiation occurs over a period of 10 minutes or less.

50. The method of claim 46, wherein the light irradiation occurs over a period of 5 minutes or less.

* * * * *